(12) United States Patent
Roeder et al.

(10) Patent No.: US 11,376,144 B2
(45) Date of Patent: Jul. 5, 2022

(54) SYSTEMS AND METHODS TO POSITION A PROSTHESIS

(71) Applicant: COOK MEDICAL TECHNOLOGIES LLC, Bloomington, IN (US)

(72) Inventors: Blayne A. Roeder, Bloomington, IN (US); Stephan Haulon, Paris (FR); Jarin Andrew Kratzberg, West Lafayette, IN (US); Kevin Wilger, Lafayette, IN (US)

(73) Assignee: COOK MEDICAL TECHNOLOGIES LLC, Bloomington, IN (US)

( * ) Notice: Subject to any disclaimer, the term of this patent is extended or adjusted under 35 U.S.C. 154(b) by 61 days.

(21) Appl. No.: 16/600,987

(22) Filed: Oct. 14, 2019

(65) Prior Publication Data

US 2020/0146859 A1 May 14, 2020

Related U.S. Application Data

(60) Provisional application No. 62/758,768, filed on Nov. 12, 2018.

(51) Int. Cl.
| | | |
|---|---|---|
| *A61F 2/966* | (2013.01) | |
| *A61F 2/07* | (2013.01) | |
| *A61F 2/06* | (2013.01) | |

(52) U.S. Cl.
CPC ............... *A61F 2/966* (2013.01); *A61F 2/07* (2013.01); *A61F 2002/061* (2013.01)

(58) Field of Classification Search
CPC ...... A61F 2/966; A61F 2/07; A61F 2002/061; A61F 2/954; A61F 2002/075; A61F 2/962
See application file for complete search history.

(56) References Cited

U.S. PATENT DOCUMENTS

| | | |
|---|---|---|
| 5,776,140 A | 7/1998 | Cottone |
| 6,143,016 A | 11/2000 | Bleam et al. |
| 6,254,609 B1 | 7/2001 | Vrba et al. |
| 7,022,133 B2 | 4/2006 | Yee et al. |
| 7,326,236 B2 | 2/2008 | Andreas et al. |
| 7,550,001 B2 | 6/2009 | Dorn et al. |
| 8,518,096 B2 | 8/2013 | Nelson |
| 8,945,202 B2 | 2/2015 | Mayberry et al. |

(Continued)

*Primary Examiner* — Todd J Scherbel
(74) *Attorney, Agent, or Firm* — Crowell & Moring LLP

(57) ABSTRACT

Systems and methods to place a prosthesis to have a preselected overlap with a receiving structure are provided. In one embodiment, a delivery system may include a primary sheath comprising a primary sheath lumen. The delivery system may further include a secondary sheath comprising a secondary sheath lumen. The primary sheath may be at least partially received within the secondary sheath lumen such that the primary sheath may translate longitudinally within the secondary sheath lumen. The delivery system may further include a prosthesis having proximal and distal ends and being received within the primary sheath lumen adjacent to the primary sheath distal end in a contracted delivery state. The delivery system may further include a length reference mechanism that indicates a length of the primary sheath distal end that extends distal to the secondary sheath distal end during the contracted delivery state of the prosthesis.

20 Claims, 27 Drawing Sheets

(56) References Cited

U.S. PATENT DOCUMENTS

| | | | |
|---|---|---|---|
| 2005/0033403 A1 | 2/2005 | Ward et al. | |
| 2007/0100422 A1* | 5/2007 | Shumer | A61F 2/966 |
| | | | 623/1.11 |
| 2007/0265694 A1* | 11/2007 | Sarac | A61F 2/95 |
| | | | 623/1.11 |
| 2009/0228015 A1* | 9/2009 | Ellis | A61B 5/1076 |
| | | | 606/87 |
| 2011/0307049 A1* | 12/2011 | Kao | A61F 2/966 |
| | | | 623/1.11 |
| 2012/0101561 A1* | 4/2012 | Porter | A61M 25/09041 |
| | | | 623/1.11 |
| 2012/0123511 A1 | 5/2012 | Brown | |
| 2013/0231736 A1 | 9/2013 | Essinger et al. | |
| 2014/0243844 A1* | 8/2014 | Clancy | A61M 37/0069 |
| | | | 606/117 |
| 2015/0265445 A1 | 9/2015 | Weber et al. | |
| 2016/0166330 A1* | 6/2016 | Lawrence | A61B 90/39 |
| | | | 606/116 |
| 2017/0056156 A1 | 3/2017 | Ryan | |

* cited by examiner

US 11,376,144 B2

SYSTEMS AND METHODS TO POSITION A PROSTHESIS

PRIORITY CLAIM

This invention claims the benefit of priority of U.S. Provisional Application Ser. No. 62/758,768, entitled "Systems and Methods to Position a Prosthesis," filed Nov. 12, 2018, the disclosure of which is hereby incorporated by reference in its entirety.

BACKGROUND

Embodiments disclosed herein generally relate to medical devices. More particularly, embodiments disclosed herein relate to medical implant delivery systems and methods, for example, systems and methods to facilitate placement of prostheses to have preselected overlaps with other prostheses and/or landing vessels.

Accurate and precise placement of a medical implant relative to one or more anatomical structures or other medical implants may improve the clinical results of a medical procedure. For example, a clinician may address a defect in a vessel by placing one or more prostheses (e.g., stents, stent-grafts, or grafts) within the vessel, e.g., to reinforce the vessel, keep the vessel open to fluid flow, connect the vessel to another prosthesis, etc. Accurate and precise placement of the prosthesis may ensure that fluid can flow in the desired manner or that the prosthesis is securely connected with the vessel or with another prosthesis. Certain characteristics of surgical procedures may however make it difficult for the clinician to accurately and precisely place a medical implant. For example, although in some surgical procedures fluoroscopy may allow the clinician to visualize the location of a medical device relative to the structure into which it is being placed, in other surgical procedures, e.g., cardiothoracic surgery, fluoroscopy may not be available to provide such guidance.

A frozen elephant trunk technique is an exemplary cardiothoracic surgery procedure in which the unavailability of fluoroscopy may make it difficult for the clinician to properly place a medical implant. A frozen elephant trunk technique may be used to treat a patient with an extensive aneurysm or dissection of the ascending aorta and descending aorta.

Other surgical procedures may present similar or different characteristics that make it difficult for a clinician to accurately and precisely place medical implants in a desired manner.

Although many different variations of medical implant placement components and procedural steps have been introduced into the art, there exists a need for designs that allow clinicians to place medical implants in an improved manner.

SUMMARY

In one aspect of the present disclosure, a delivery system may be provided. The delivery system includes a primary sheath extending from a primary sheath distal end to a primary sheath proximal end and comprising a primary sheath lumen from the primary sheath distal end to the primary sheath proximal end. A secondary sheath extends from a secondary sheath distal end to a secondary sheath proximal end and comprises a secondary sheath lumen from the secondary sheath distal end to the secondary sheath proximal end. The primary sheath is at least partially received within the secondary sheath lumen such that the primary sheath translates longitudinally within the secondary sheath lumen. The delivery system further includes a prosthesis having proximal and distal ends and being received within the primary sheath lumen adjacent to the primary sheath distal end in a contracted delivery state. A length reference mechanism is disposed at the secondary sheath proximal end. The length reference mechanism indicates a length of the primary sheath distal end that extends distal to the secondary sheath distal end during the contracted delivery state of the prosthesis.

In a second aspect of the present disclosure, a delivery system may be provided. The delivery system includes a primary sheath extending from a primary sheath distal end to a primary sheath proximal end and comprising a primary sheath lumen from the primary sheath distal end to the primary sheath proximal end. The delivery system further includes a secondary sheath extending from a secondary sheath distal end to a secondary sheath proximal end and comprising a secondary sheath lumen from the secondary sheath distal end to the secondary sheath proximal end. The primary sheath is at least partially received within the secondary sheath lumen such that the primary sheath translates longitudinally within the secondary sheath lumen. The delivery system has a loaded configuration in which a prosthesis having proximal and distal ends is received within the primary sheath lumen adjacent to the primary sheath distal end in a contracted delivery state. The delivery system further includes a length reference mechanism disposed at the secondary sheath proximal end. The length reference mechanism indicates a length of the primary sheath distal end that extends distal to the secondary sheath distal end during the contracted delivery state of the prosthesis. The delivery system further includes a sheath-locking mechanism that selectively locks the primary sheath to the secondary sheath such that longitudinal proximal translation of the primary sheath causes longitudinal proximal translation of the secondary sheath.

In a third aspect of the present disclosure, a method to place a prosthesis to have a preselected overlap with a receiving structure may be provided. The method includes providing a primary sheath, a secondary sheath, and the prosthesis, where the primary sheath extends from a primary sheath distal end to a primary sheath proximal end and comprises a primary sheath lumen from the primary sheath distal end to the primary sheath proximal end. The secondary sheath extends from a secondary sheath distal end to a secondary sheath proximal end and comprises a secondary sheath lumen from the secondary sheath distal end to the secondary sheath proximal end. The prosthesis has proximal and distal ends and is received within the primary sheath lumen adjacent to the primary sheath distal end in a contracted delivery state. The distal end of the secondary sheath is disposed adjacent to a proximal end of a receiving lumen that is defined by the receiving structure. The primary sheath is disposed within the secondary sheath lumen such that a length reference mechanism disposed at the secondary sheath proximal end indicates a length of the primary sheath distal end that extends distal to the secondary sheath distal end during the contracted delivery state of the prosthesis. The length corresponds to the preselected overlap with the receiving structure. The method further includes longitudinally translating the primary sheath and the secondary sheath proximally relative to the prosthesis to transition the prosthesis from the contracted delivery state to an expanded deployed state in which the prosthesis is received within the receiving lumen and has the preselected overlap with the receiving structure.

Other systems, methods, features and advantages of the invention will be, or will become, apparent to one with skill in the art upon examination of the following figures and detailed description. It is intended that all such additional systems, methods, features and advantages be within the scope of the invention, and be encompassed by the following claims.

BRIEF DESCRIPTION OF THE DRAWINGS

The invention can be better understood with reference to the following drawings and description. The components in the figures are not necessarily to scale, emphasis instead being placed upon illustrating the principles of the invention. Moreover, in the figures, like referenced numerals designate corresponding parts throughout the different views.

FIG. 9 is locked together with and simultaneously partially retracted with the secondary sheath assembly of the delivery system of FIG. 3 or FIG. 9;

DETAILED DESCRIPTION OF THE PREFERRED EMBODIMENTS

In the present application, the term "proximal" refers to a direction that is generally closest to the heart during a medical procedure, while the term "distal" refers to a direction that is furthest from the heart during a medical procedure.

Aspects and embodiments of the present disclosure are configured to address a need for designs that provide clinicians with more accurate and more precise medical implant placement, and in doing so, they may provide various benefits. For example, aspects and embodiments of the present disclosure may provide for accurate and precise prosthesis placement by allowing for the surgeon to know the length of the prosthesis that is in a landing vessel, despite the unavailability of fluoroscopy or other imaging modalities for visualization of the prosthesis or landing vessel. Aspects and embodiments of the present disclosure may provide for accurate and precise prosthesis placement by ensuring a preselected overlap between a connection prosthesis, a branch of another prosthesis, and a landing vessel. Aspects and embodiments of the present disclosure may provide for accurate and precise prosthesis placement using a delivery system that can flex during placement in order to track through a main body prosthesis or the patient's body to the delivery location. Aspects and embodiments of the present disclosure may provide for simple manufacturing, by allowing for manufacturing of one length of sheath, pusher, and/or cannula, for all lengths of connection prostheses. Those of skill in the art, having the benefit of the present disclosure, may recognize that aspects and embodiments of the present disclosure solve additional problems, provide additional benefits, and may, within the scope of the present disclosure, be practiced in additional technological environments, including during the placement of a variety of medical implants other than prostheses, and during the placement of medical implants using procedures other than a frozen elephant trunk technique.

Figure 1:
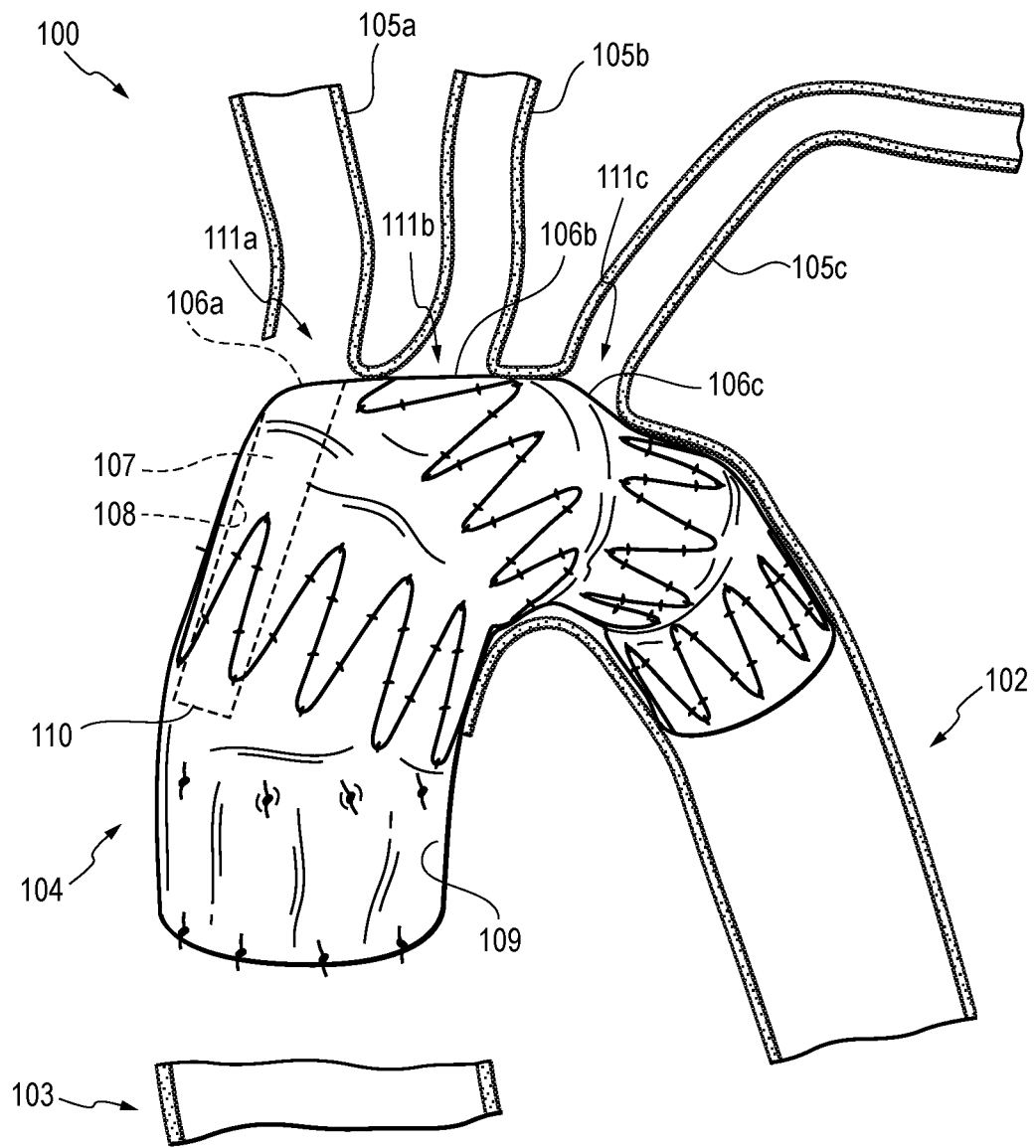
FIG. 1 is a partial sectional view of a partially completed frozen elephant trunk procedure.
Figure 2:
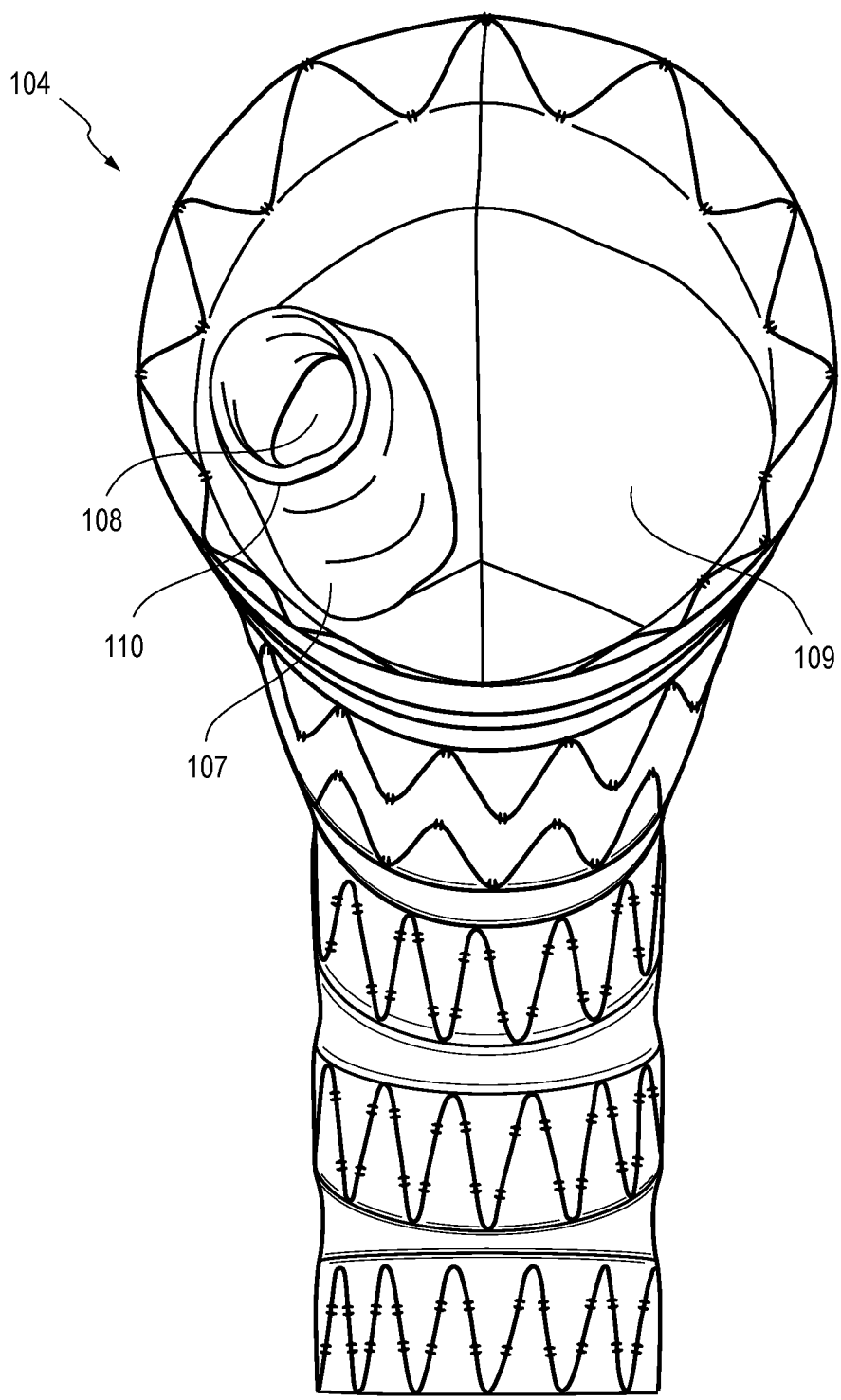
FIG. 2 is a perspective view of a main body prosthesis with an internal branch as also shown in FIG. 1.

An exemplary environment 100 in which a frozen elephant trunk technique has been partially performed is described with reference to FIGS. 1 and 2. A frozen elephant trunk technique may generally involve: (a) dividing the ascending aorta from the aortic arch 101, the descending aorta 102, and the aortic root 103; (b) placing a first portion of a main body prosthesis 104 within the internal lumen of the descending aorta 102 such that a second portion of the main body prosthesis 104 extends toward the aortic root 103; (c) connecting an end of the first portion of the main body prosthesis 104 to the descending aorta 102; (d) connecting the main body prosthesis 104 to one or more vessels (e.g., brachiocephalic artery 105a, left common carotid artery 105b, and left subclavian artery 105c) that are attached to the roof of the aortic arch 101; and (e) connecting an end of the second portion of the main body prosthesis 104 to the aortic root 103. In FIG. 1, steps (a)-(c) have been performed.

In the frozen elephant trunk technique, connections of the main body prosthesis 104 to the descending aorta 102 and aortic root 103 may be achieved through anastomoses, while connections of the main body prosthesis 104 to the vessels 105a, 105b, 105c attached to the roof of the aortic arch 101 may be achieved using connection prostheses. The main body prosthesis 104 may include fenestrations 106a, 106b, 106c in its wall, located between the end of the main body prosthesis 104 that will be connected to the aortic root 103 and the end of the main body prosthesis 104 connected to the descending aorta 102, with each fenestration 106a, 106b, 106c corresponding to a respective one of the vessels 105a, 105b, 105c that are attached to the roof of the aortic arch 101. Branch vessel ostia, e.g., ostium 111a, ostium 111b, ostium 111c, are disposed along the aortic arch 101.

The main body prosthesis 104 may also include a plurality of internal or external branches to facilitate connection, with each branch comprising a generally tubular structure connected at and extending from its corresponding fenestration. For example, in FIGS. 1 and 2, an internal branch 107 extends inward into the main body prosthesis 104 from its corresponding fenestration 106a and comprises a receiving lumen 108. In some main body prostheses, an external branch would extend out of the main body prosthesis from its corresponding fenestration. Branches extending from fenestrations 106b and 106c have been omitted to provide a clearer illustration. A branch, e.g., internal branch 107, may be adapted to receive within its lumen, e.g., receiving lumen 108, an expandable connection prosthesis, such that one end of the connection prosthesis is placed in the branch and an opposite end of the connection prosthesis extends out from the main body prosthesis and is received within the given vessel, e.g., 105a. When the connection prosthesis is properly placed within the branch and the given vessel, the connection prosthesis can be expanded to achieve a desired connection of the main body prosthesis to that vessel.

Properly placing a connection prosthesis within a branch and vessel may include establishing a preselected overlap between the connection prosthesis, the vessel, and the branch. For example, for a main body prosthesis that includes internal branches, a preselected overlap may be one in which a preselected length of connection prosthesis is within a vessel. Additionally or alternatively, for a main body prosthesis that includes internal branches, a preselected overlap may be one in which a proximal edge of a connection prosthesis is coincident with a proximal edge of the internal branch into which it is placed. However, it may be difficult for the clinician to align the proximal edge of the connection prosthesis and the proximal edge of the internal branch, because the proximal edge of the internal branch may be surrounded by the primary main body prosthesis and thus not visible to the clinician, and because fluoroscopy may not be available to assist in visualization. Additionally or alternatively, for similar reasons, it may be difficult for the clinician to determine whether a sufficient length of connection prostheses has landed within a vessel.

Figure 3:
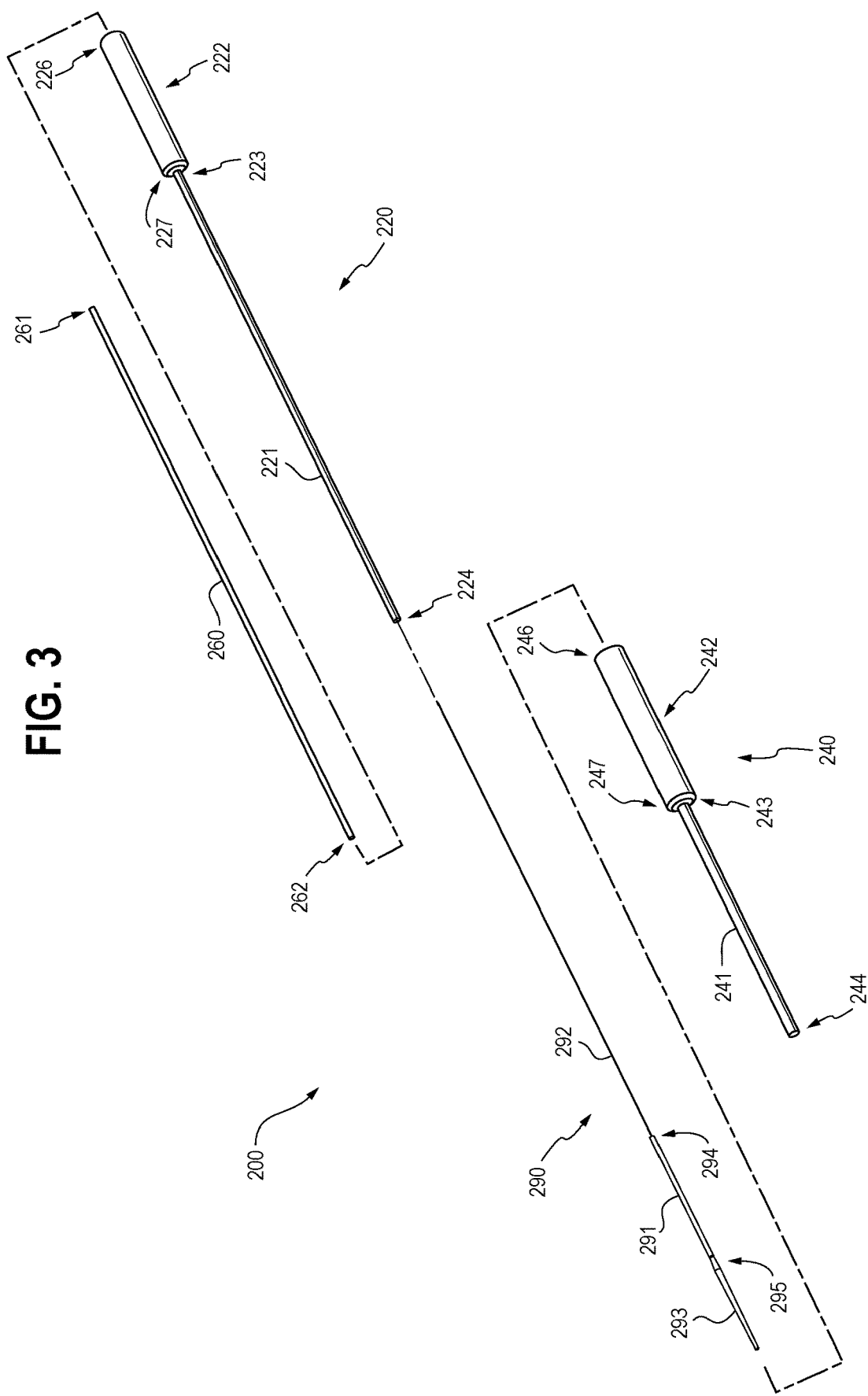
FIG. 3 is an exploded view of a first delivery system.
Figure 4:
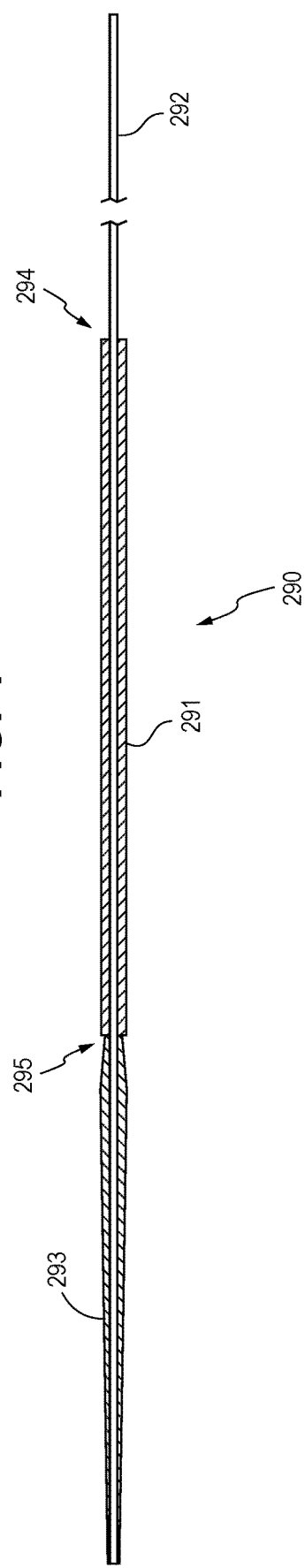
FIG. 4 is a longitudinal cross-sectional view through a connection prosthesis assembly of the delivery systems of FIGS. 3 and 9.
Figure 5:
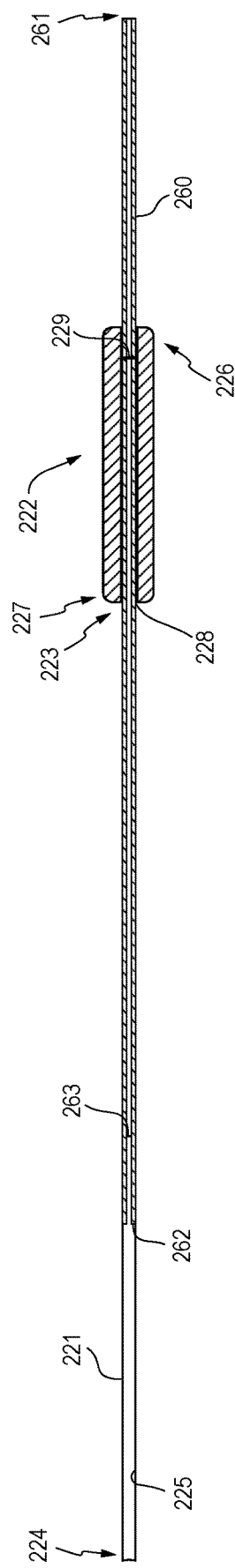
FIG. 5 is a longitudinal cross-sectional view through a primary sheath assembly of the delivery system of FIG. 3 receiving a pusher of the delivery system of FIG. 3.
Figure 6:
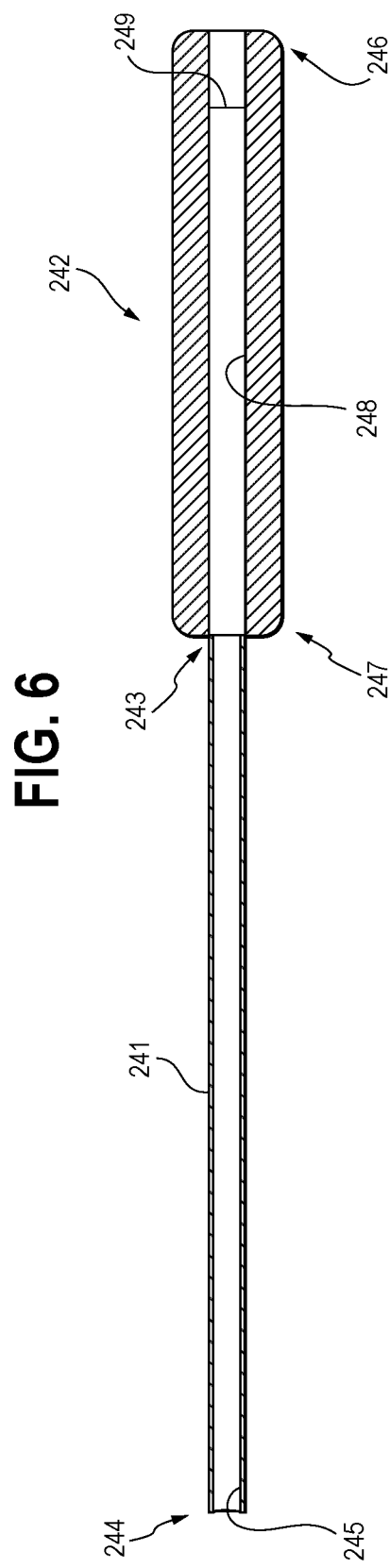
FIG. 6 is a longitudinal cross-sectional view through a secondary sheath assembly of the delivery system of FIG. 3.
Figure 7:
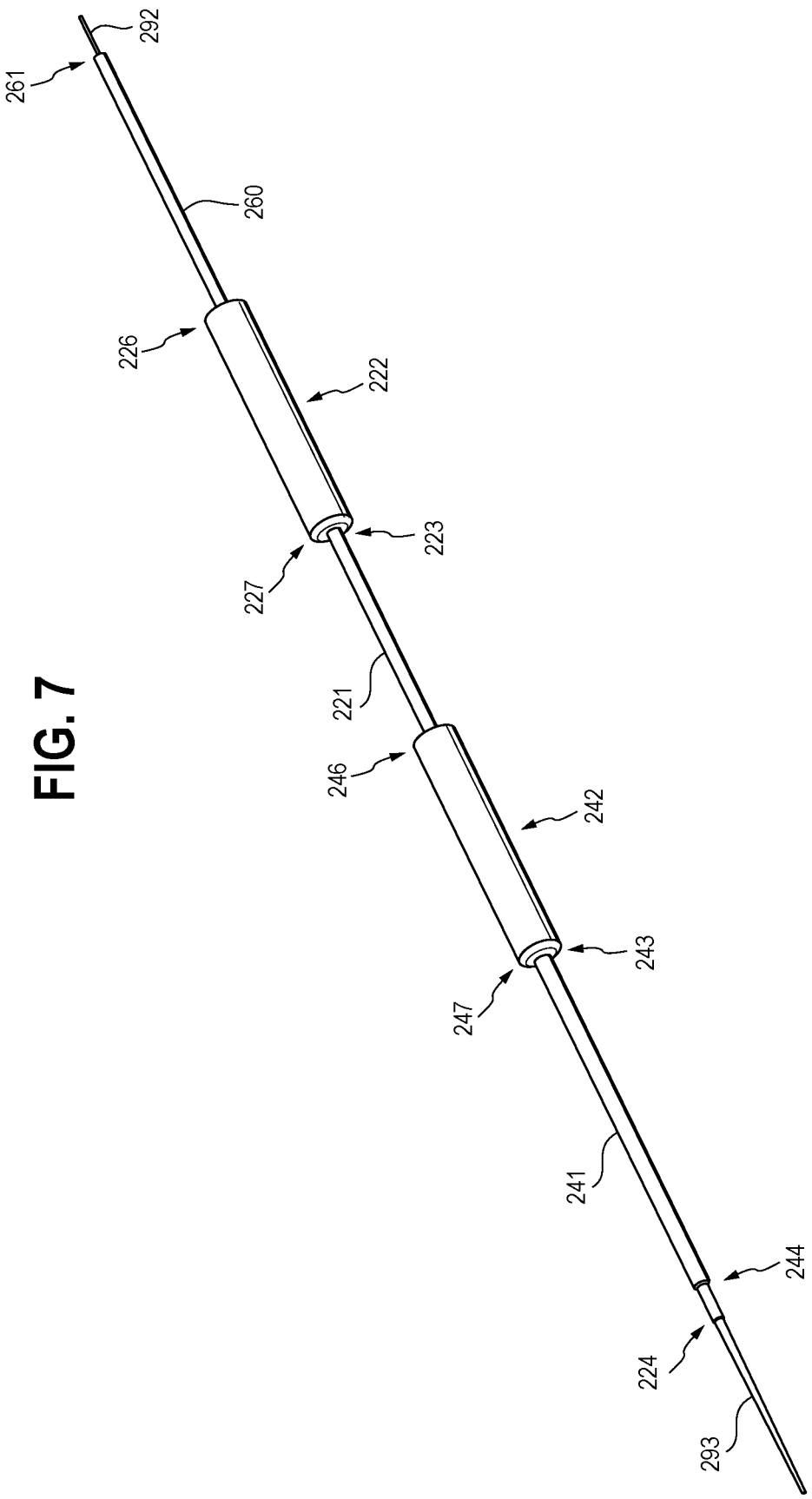
FIG. 7 is a perspective view of the delivery system of FIG. 3 in a first state indicating that a preselected overlap has not been established.

Embodiments of a first medical implant delivery system and associated methods are described with reference to FIGS. 3-8, 14A-14G, 15A, 15B, 18A, 18B, and 19A-19C, which illustrate delivery system 200 and associated methods. As illustrated for example in an exploded view in FIG. 3 and perspective views in FIGS. 7 and 8, delivery system 200 includes primary sheath assembly 220, secondary sheath assembly 240, pusher 260, and length reference mechanism 280. Delivery system 200 further includes, or is adapted for use with, connection prosthesis assembly 290.

Connection prosthesis assembly 290 is illustrated for example in FIGS. 3, 4, 7, 8, 9, and 13, and includes connection prosthesis 291, cannula 292, and tip 293. Connection prosthesis 291 extends from connection prosthesis proximal end 294 to connection prosthesis distal end 295. Connection prosthesis 291 has a contracted delivery state and an expanded deployment state, and surrounds a distal portion of cannula 292. Cannula 292 comprises a cannula lumen through its length, through which a guidewire may longitudinally translate. Tip 293 comprises a tip lumen through its length, through which the guidewire may also longitudinally translate.

Primary sheath assembly 220 is illustrated for example in FIGS. 3, 5, 7, and 8, and generally retains connection prosthesis 291 and delivers it to the appropriate placement in a landing vessel and main body prosthesis. Primary sheath assembly 220 includes primary sheath 221 and primary valve assembly 222.

Primary sheath 221 comprises a generally tubular elongated structure extending from primary sheath proximal end 223 to primary sheath distal end 224 and comprising primary sheath lumen 225. Primary sheath 221 may for example comprise a FLEXOR® Sheath, which is available from Cook Incorporated, Bloomington, Ind., USA, or any other suitable structure. Primary sheath lumen 225 is adapted to receive and retain connection prosthesis assembly 290 with connection prosthesis 291 in the contracted delivery state, while still allowing primary sheath assembly 220 to longitudinally translate relative to connection prosthesis 291 for deployment.

Primary valve assembly 222 extends from primary valve assembly proximal end 226 to primary valve assembly distal end 227. Primary valve assembly distal end 227 is coupled to primary sheath proximal end 223. Primary valve assembly 222 comprises primary valve assembly lumen 228, within which primary valve 229 is disposed.

Pusher 260 is illustrated for example in FIGS. 3, 5, 7, and 8, and generally serves to push connection prosthesis 291 out of primary sheath 221. Pusher 260 is a generally tubular elongated structure extending from pusher proximal end 261 to pusher distal end 262 and comprising pusher lumen 263. Pusher 260 is adapted to be received in and longitudinally translate relative to primary sheath lumen 225 and primary valve lumen 228. During a procedure, primary valve 229 sealingly engages pusher 260 to control blood loss. An exemplary suitable hemostatic valve assembly for primary valve assembly 222 is the CAPTOR® Hemostatic Valve, which is available from Cook Incorporated, Bloomington, Ind., USA. Pusher lumen 263 is adapted to receive cannula 292 of connection prosthesis assembly 290, such that when delivery system 200 is assembled, pusher distal end 262 is disposed adjacent to or abutting connection prosthesis proximal end 294.

Secondary sheath assembly 240 is illustrated for example in FIGS. 3, 6, 7, and 8, and generally serves as a reference point for the length of connection prosthesis 291 that is received in the landing vessel. Secondary sheath assembly includes secondary sheath 241 and secondary valve assembly 242.

Secondary sheath 241 is a generally tubular elongated structure extending from secondary sheath proximal end 243 to secondary sheath distal end 244 and comprising secondary sheath lumen 245. Secondary sheath 241 may for example comprise a FLEXOR® Sheath, which is available from Cook Incorporated, Bloomington, Ind., USA, or any other suitable structure.

Secondary valve assembly 242 extends from secondary valve assembly proximal end 246 to secondary valve assembly distal end 247. Secondary valve assembly distal end 247 is coupled to secondary sheath proximal end 243. Secondary valve assembly 242 comprises secondary valve assembly lumen 248, within which secondary valve 249 is disposed.

Primary sheath 221 is adapted to longitudinally translate within secondary sheath lumen 245 and secondary valve assembly lumen 248 such that primary sheath 221 can longitudinally translate relative to secondary sheath assembly 240. During a procedure, secondary valve 249 sealingly engages primary sheath 221 to control blood loss. An exemplary suitable hemostatic valve assembly for secondary valve assembly 242 is the CAPTOR® Hemostatic Valve, which is available from Cook Incorporated, Bloomington, Ind., USA.

Figure 8:
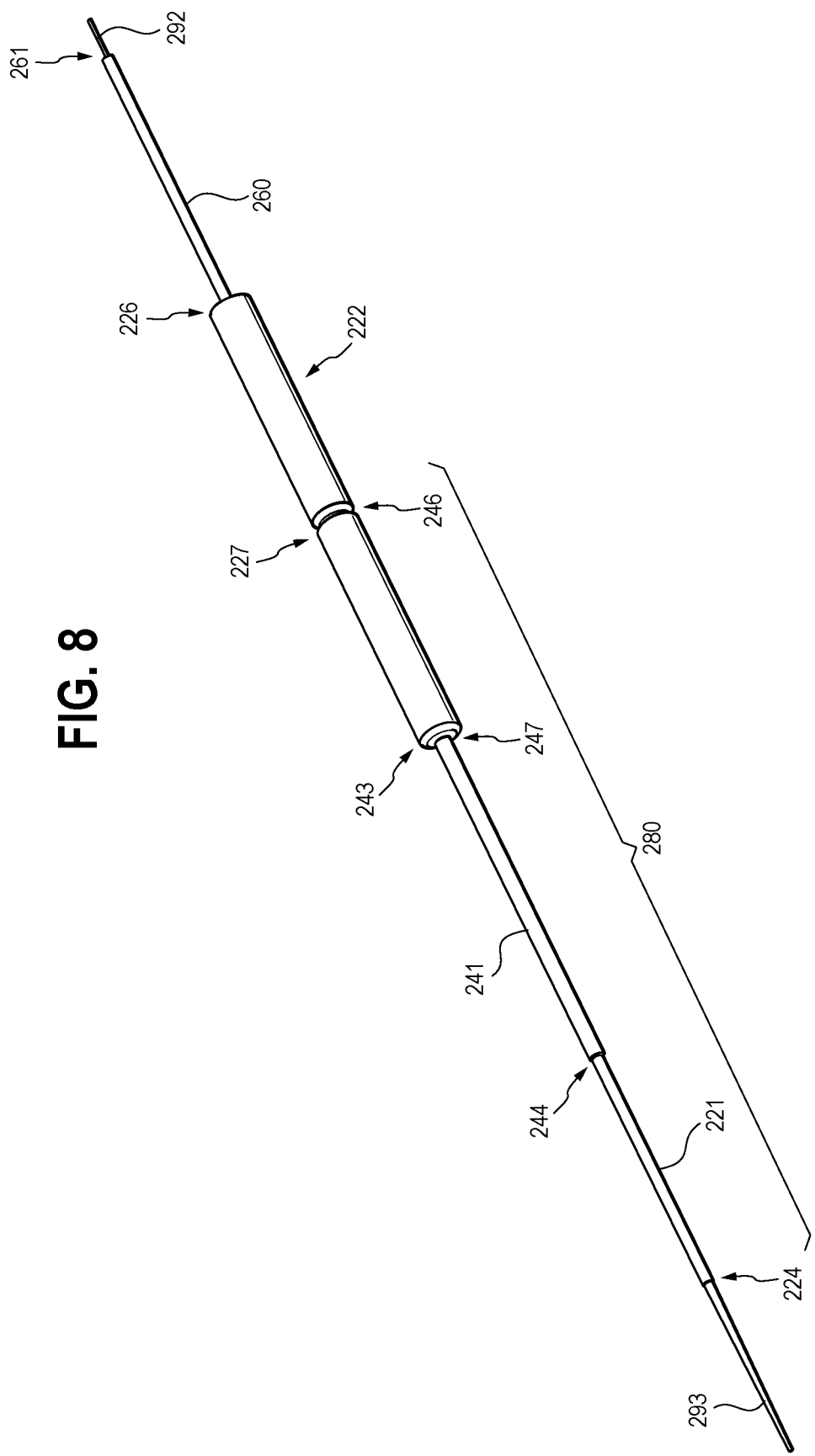
FIG. 8 is a perspective view of the delivery system of FIG. 3 in a second state indicating that a preselected overlap has been established.
Figure 9:
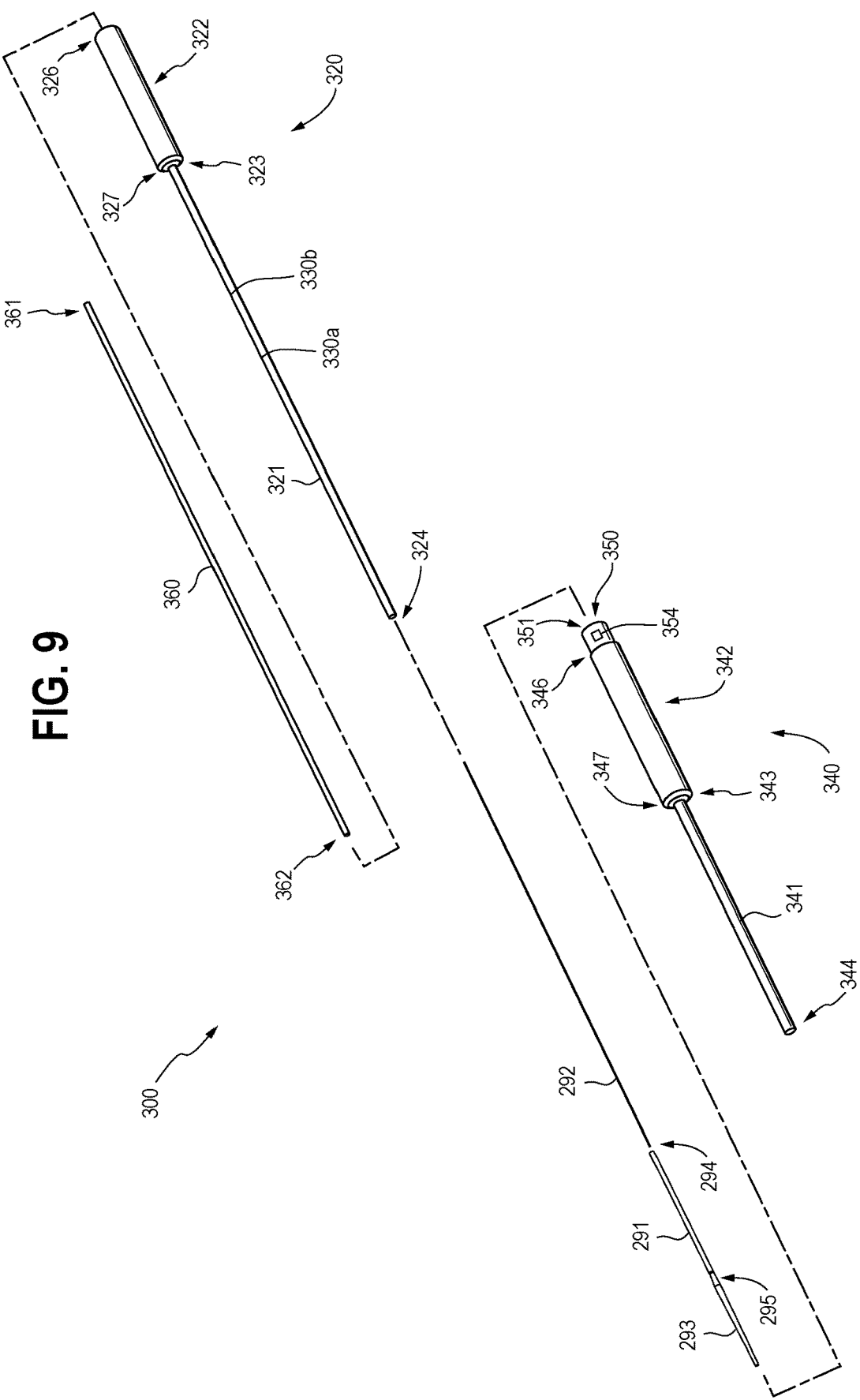
FIG. 9 is an exploded view of a second delivery system.
Figure 10:
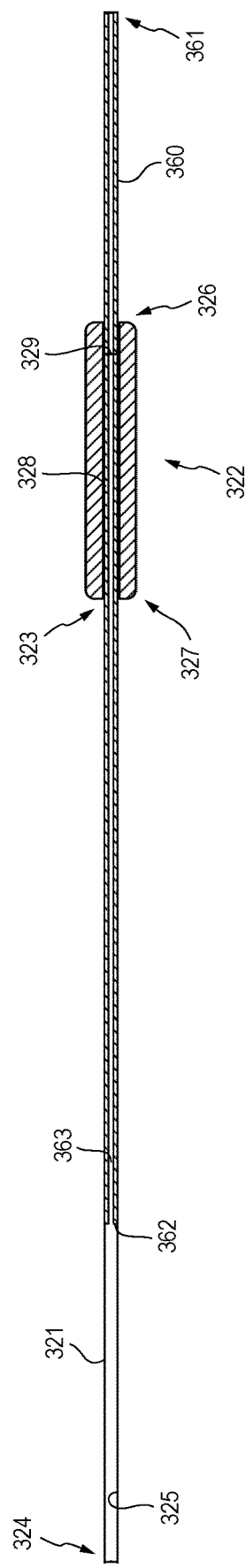
FIG. 10 is a longitudinal cross-sectional view through a primary sheath assembly of the delivery system of FIG. 9 receiving a pusher of the delivery system of FIG. 9.
Figure 11:
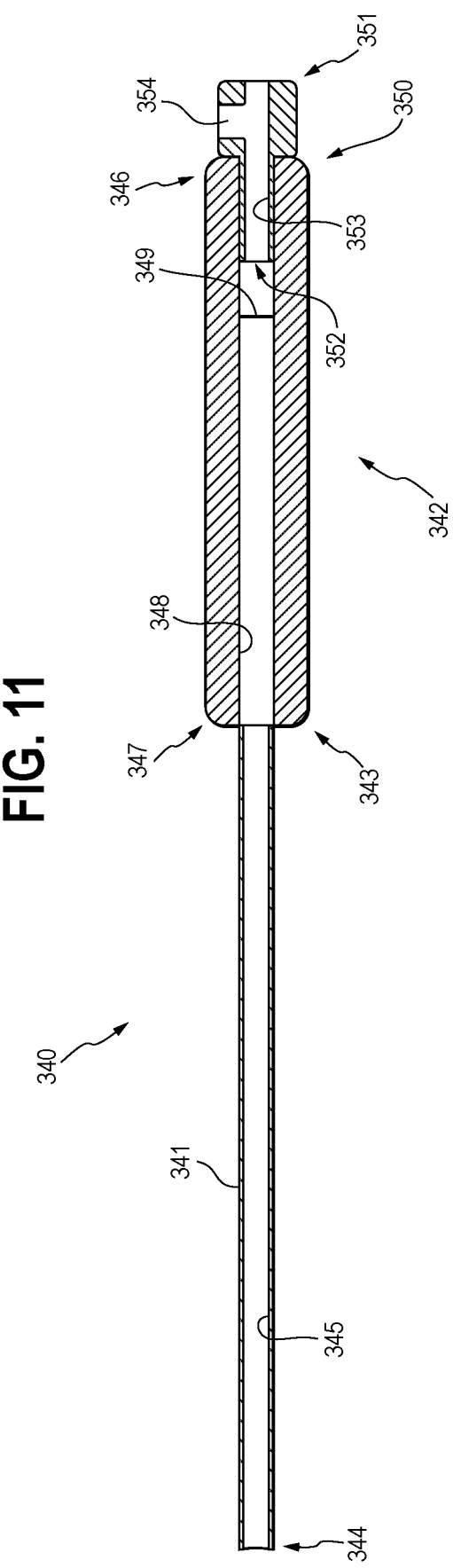
FIG. 11 is a longitudinal cross-sectional view through a secondary sheath assembly of the delivery system of FIG. 9.

Length reference mechanism 280, as depicted in FIG. 8, is provided by selecting primary sheath 221 and secondary sheath assembly 240 so that primary sheath 221 has a total length between primary sheath proximal end 223 and primary sheath distal end 224 that ensures that a desired preselected length of connection prosthesis 291 will be within and overlapping with the landing vessel when, at a same time: (a) secondary sheath distal end 244 is positioned at the ostium of the landing vessel; and (b) primary sheath 221 is received within secondary sheath lumen 245 so that primary valve assembly distal end 227 contacts secondary valve assembly proximal end 246. Length reference mechanism 280 may be provided by selecting primary sheath 221 to have a total length between primary sheath proximal end 223 and primary sheath distal end 224 that equals: (the total length between secondary sheath distal end 244 and secondary valve assembly proximal end 246) plus (the total length between connection prosthesis distal end 295 and connection prosthesis 294) plus (the total desired length of longitudinal overlap of primary sheath 221 with tip 293) plus (the total length of the internal branch with which delivery system 200 will be used, e.g., the total length of internal branch 107 between fenestration 106*a* and inner branch proximal end 110). In length reference mechanism 280, primary valve assembly distal end 227 acts as an indicator of a length of primary sheath 221 extending distal to secondary sheath distal end 244. Further, when connection prosthesis 291 is received in primary sheath 221 in the manner described above, primary valve assembly distal end 227 acts as an indicator that the desired preselected length of connection prosthesis 291 is within and overlapping with the landing vessel. The manner in which length reference mechanism 280 allows the clinician to ensure that the desired preselected length of connection prosthesis 291 is within and overlapping with the landing vessel is described in further detail in connection with methods described below with reference to FIGS. 7, 8, 14A-14G, 18A, 18B, and 19A-19C.

In some embodiments, a minimum total length of pusher 260 between pusher proximal end 261 and pusher distal end 262 may be selected to equal: (the total length between primary sheath distal end 224 and primary valve assembly proximal end 226) minus (the total desired length of longitudinal overlap of primary sheath 221 with tip 293).

Figure 12:
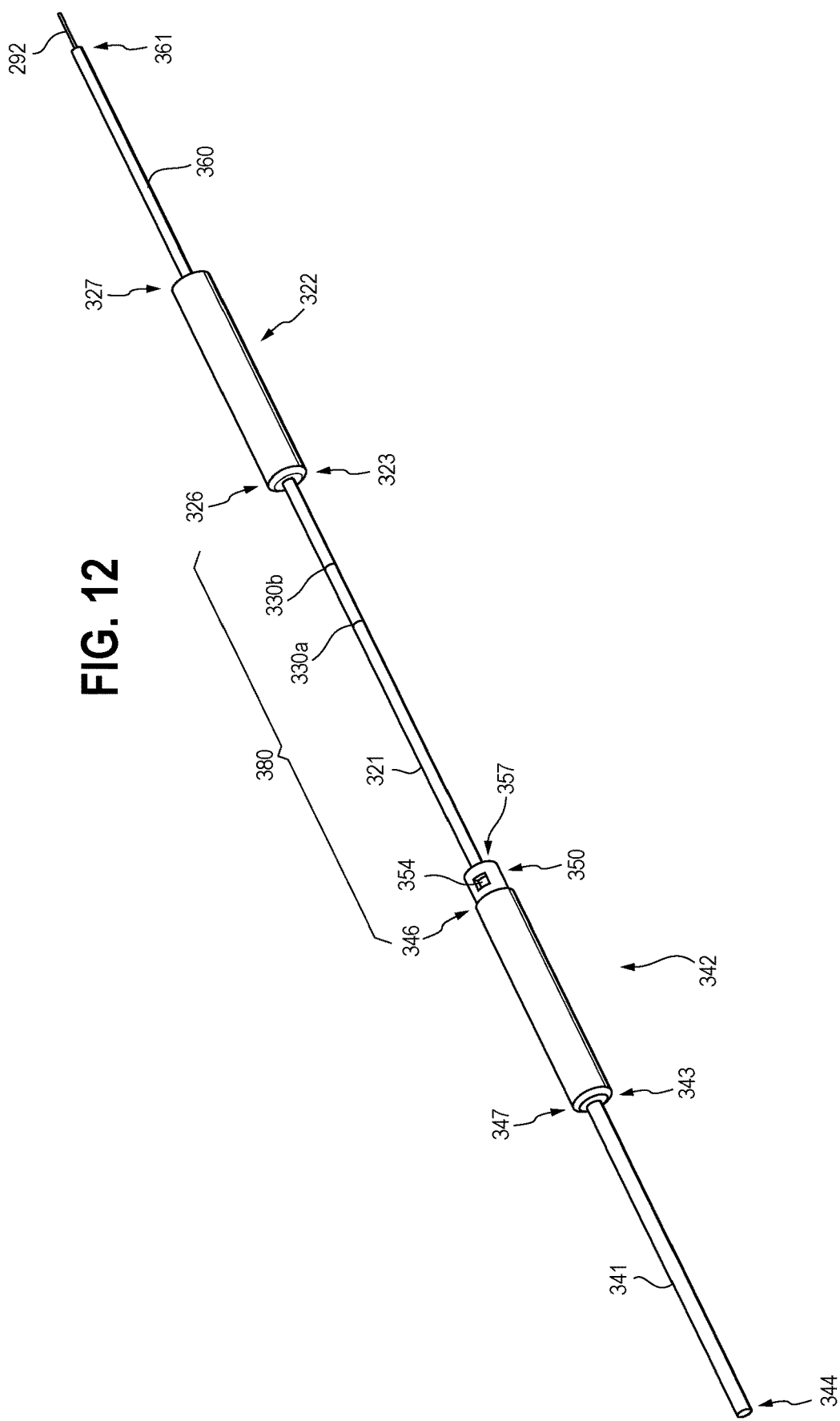
FIG. 12 is a perspective view of the delivery system of FIG. 9 in a first state indicating that a preselected overlap has not been established.

Embodiments of a second medical implant delivery system and associated methods are described with reference to FIGS. 4, 9-13, 14A-14G, 15A-15B, 16A, 17A-17B, 18A-18B, and 19A-19C, which illustrate delivery system 300 and associated methods. As illustrated for example in an exploded view in FIG. 9 and perspective views in FIGS. 12 and 13, delivery system 300 includes primary sheath assembly 320, secondary sheath assembly 340, pusher 360, and length reference mechanism 380. Delivery system 300 further includes, or is adapted for use with, connection prosthesis assembly 290.

Primary sheath assembly 320 is illustrated for example in FIGS. 9, 10, 12, and 13, and includes primary sheath 321 and primary valve assembly 322.

Primary sheath 321 is a generally tubular elongated structure extending from primary sheath proximal end 323 to primary sheath distal end 324 and comprising primary sheath lumen 325. Primary sheath 321 may for example comprise a FLEXOR® Sheath, which is available from Cook Incorporated, Bloomington, Ind., USA, or any other suitable structure. Primary sheath lumen 325 is adapted to receive and retain connection prosthesis assembly 290 with connection prosthesis 291 in the contracted delivery state, while still allowing primary sheath assembly 320 to longitudinally translate relative to connection prosthesis 291 for deployment.

Primary valve assembly 322 extends from primary valve assembly proximal end 326 to primary valve assembly distal end 327. Primary valve assembly distal end 327 is coupled to primary sheath proximal end 323. Primary valve assembly 322 comprises primary valve assembly lumen 328, within which primary valve 329 is disposed.

Pusher 360 is illustrated for example in FIGS. 9, 10, 12, and 13, and is a generally tubular elongated structure extending from pusher proximal end 361 to pusher distal end 362 and comprising pusher lumen 363. Pusher 360 is adapted to be received within primary sheath lumen 325 and primary valve lumen 328. During a procedure, primary valve 329 sealingly engages pusher 360 to control blood loss. An exemplary suitable hemostatic valve assembly for primary valve assembly 322 is the CAPTOR® Hemostatic Valve, which is available from Cook Incorporated, Ind., USA. Pusher lumen 363 is adapted to receive cannula 292 of connection prosthesis assembly 290, such that when delivery system 300 is assembled, pusher distal end 362 is disposed adjacent to or abutting connection prosthesis proximal end 294.

Secondary sheath assembly 340 is illustrated for example in FIGS. 9 and 11-13, and includes secondary sheath 341 and secondary valve assembly 342.

Secondary sheath 341 is a generally tubular elongated structure extending from secondary sheath proximal end 343 to secondary sheath distal end 344 and comprising secondary sheath lumen 345. Secondary sheath 341 may for example comprise a FLEXOR® Sheath, which is available from Cook Incorporated, Bloomington, Ind., USA, or any other suitable structure.

Secondary valve assembly 342 extends from secondary valve assembly proximal end 346 to secondary valve assembly distal end 347. Secondary valve assembly distal end 347 is coupled to secondary sheath proximal end 343. Secondary valve assembly 342 comprises secondary valve assembly lumen 348, within which secondary valve 349 is disposed.

Secondary valve assembly 342 further includes indicator window assembly 350. Indicator window assembly 350 extends from indicator window assembly proximal end 351 to indicator window assembly distal end 352 and comprises indicator window assembly lumen 353 therebetween. Indicator window assembly 350 further comprises indicator window 354, which extends radially inward from an outer surface of indicator window assembly 350 towards indicator window assembly lumen 353. Indicator window 354 allows for an outer surface of primary sheath 321 to be observed therethrough when primary sheath 321 is received within indicator window assembly lumen 353. An exemplary implementation of indicator window 354 is an aperture extending radially from the outer surface of primary sheath 321 to indicator window assembly lumen 353. In some embodiments, the aperture may be at least partially filled with a transparent structure.

Primary sheath 321 is adapted to longitudinally translate through secondary sheath lumen 345, secondary valve assembly lumen 348, and indicator window lumen 353 such that primary sheath 321 can longitudinally translate relative to secondary sheath assembly 340. During a procedure, secondary valve 349 sealingly engages primary sheath 321 to control blood loss. An exemplary suitable hemostatic valve assembly for secondary valve assembly 342 is the CAPTOR® Hemostatic Valve, which is available from Cook Incorporated, Bloomington, Ind., USA.

Primary sheath 321 further includes one or more indicia disposed on, at, or in its outer surface. For example, indicia 330a, 330b, are disposed in a longitudinally spaced manner on the outer surface of primary sheath 321. The indicia may be applied by printing or any other suitable process. When primary sheath 321 is longitudinally translated through indicator window lumen 354 such that one of the indicia is longitudinally aligned with indicator window 354, that indicia is visible through indicator window 354. The respective longitudinal positions of the indicia are calibrated such that when a given indicia is longitudinally aligned with indicator window lumen 354, that indicia indicates the length of primary sheath 321 that extends distal to secondary sheath distal end 344. The calibration may for example be accomplished by: (1) determining the longitudinal distance, L, between indicator window 354 and secondary sheath distal end distal end 344; (2) setting a point on primary sheath 321 that is located proximally from primary sheath distal end 324 by longitudinal distance L as the zero point; (3) setting a point, p, that is proximal to the zero point on primary sheath 321 as indicating that a length of primary sheath 321 that extends distal to secondary sheath distal end 344 when point p is visible in indicator 354 is equal to point p's distance from the zero point; and (4) applying an indicia at point p. The calibration may be repeated to add as many indicia as suitable to primary sheath 321.

In one exemplary implementation of a calibrated primary sheath 321, when indicia 330a is visible through indicator window 354, this indicates that 56 millimeters of connection stent 291 extends distal to secondary sheath distal end 344, while when indicia 330b is visible through indicator 354, this indicates that 90 millimeters of connection stent 291 extends distal to secondary sheath distal end 344. The indicia may represent the length of primary sheath 321 that extends distal to secondary sheath distal end 344 in any suitable manner. The indicia may for example be a numerical representation of the length of connection stent 291 that extends distal to secondary sheath distal end 344. For example, indicia 330a may be the number "56" printed on the outer surface of primary sheath 321 and indicia 330b may be the number "90" printed on the outer surface of primary sheath 321. These particular lengths and manners of representing them are however merely exemplary.

The combination of indicator window assembly 350 and indicia, e.g., indicia 330a, 330b, provides length reference mechanism 380. When connection prosthesis 291 is received in primary sheath 321 in the contracted delivery state in the manner discussed above, length reference mechanism 380 allows the clinician to use delivery system 300 to ensure that a desired preselected length of connection prosthesis 291 is in the landing vessel. The manner in which length reference mechanism 380 allows the clinician to do so is described in further detail in connection with methods described below with reference to FIGS. 12, 13, 14A-14G, 18A, 18B, and 19A-19C.

Additionally, given the design of delivery system 300, particularly the inclusion along the length of primary sheath 321 of a plurality of indicia, e.g., 330a, 330b, and the ability of various components (e.g., pusher 360 and secondary sheath assembly 340) to longitudinally translate relative to each other, delivery system 300 may provide for simple manufacturing, as primary sheath 321, secondary sheath 341, pusher 360, and cannula 392 can each be made with a single respective length that allows delivery system 300 to be used for all lengths of connection prosthesis.

FIGS. 14A-14G depict an environment similar to the exemplary environment 100 of FIG. 1, but add a cross-sectional view through main body prosthesis 104 and show delivery systems 200 or 300 in various states during an exemplary frozen elephant trunk procedure. In view of structural and functional similarities between distal portions of delivery systems 200 and 300, FIGS. 14A-14G, 18A, 18B, and 19A-19C, and the portions of the specification related thereto, refer to corresponding aspects of delivery systems 200 and 300 in the alternative. For example, where the specification uses the terminology "secondary sheath 241, 341," or a reference line in FIGS. 14A-14G, 18A, 18B, and 19A-19C points to "241, 341," this indicates that the secondary sheath depicted in FIGS. 14A-14G, 18A, 18B, and 19A-19C can be secondary sheath 241 or secondary sheath 341.

Figure 14A:
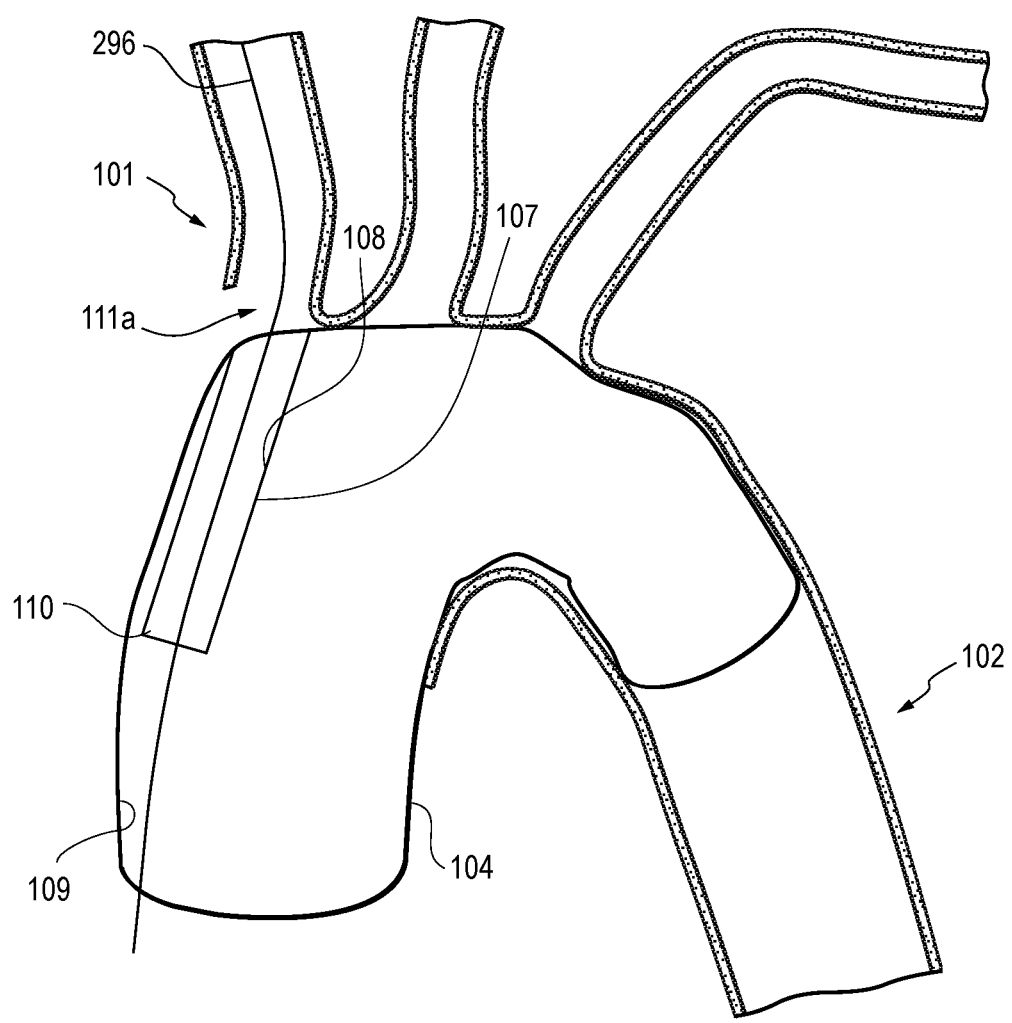
FIGS. 14A-14G are partial cross-sectional views depicting various stages of completion of an exemplary frozen elephant trunk procedure.

In FIG. 14A, guidewire 296 has been guided through curved lumen 109 of main body prosthesis 104, through receiving lumen 108 of internal branch 107, and into brachiocephalic artery 105a.

Figure 14B:
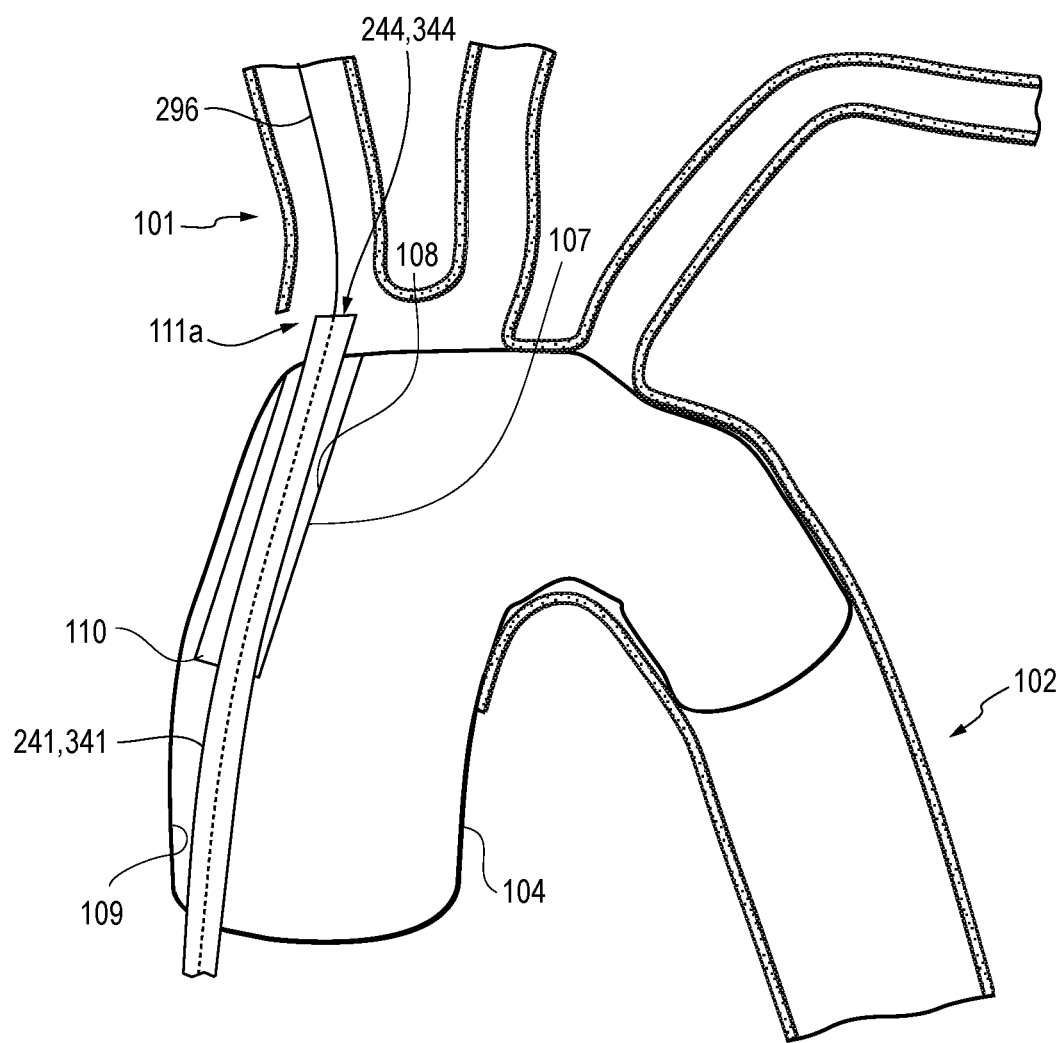

In FIG. 14B, secondary sheath 241, 341 has been inserted over guidewire 296, with guidewire 296 received in secondary sheath lumen 245, 345, until secondary sheath distal end 244, 344 is disposed at or adjacent to ostium 111a of brachiocephalic artery 105a (i.e., the exemplary landing vessel). Because the exemplary frozen elephant trunk procedure is at least in part an open procedure, the clinician can visually verify that secondary sheath distal end 244, 344 has reached this position. Secondary sheath distal end 244, 344 is then able to serve as a reference point for the length of primary sheath 221, 321 that extends distal to secondary sheath distal end 244, 344, and consequently as a reference point for the length of connection prosthesis 291 that is received in the lumen of brachiocephalic artery 105a and overlaps with brachiocephalic artery 105a.

Figure 14C:
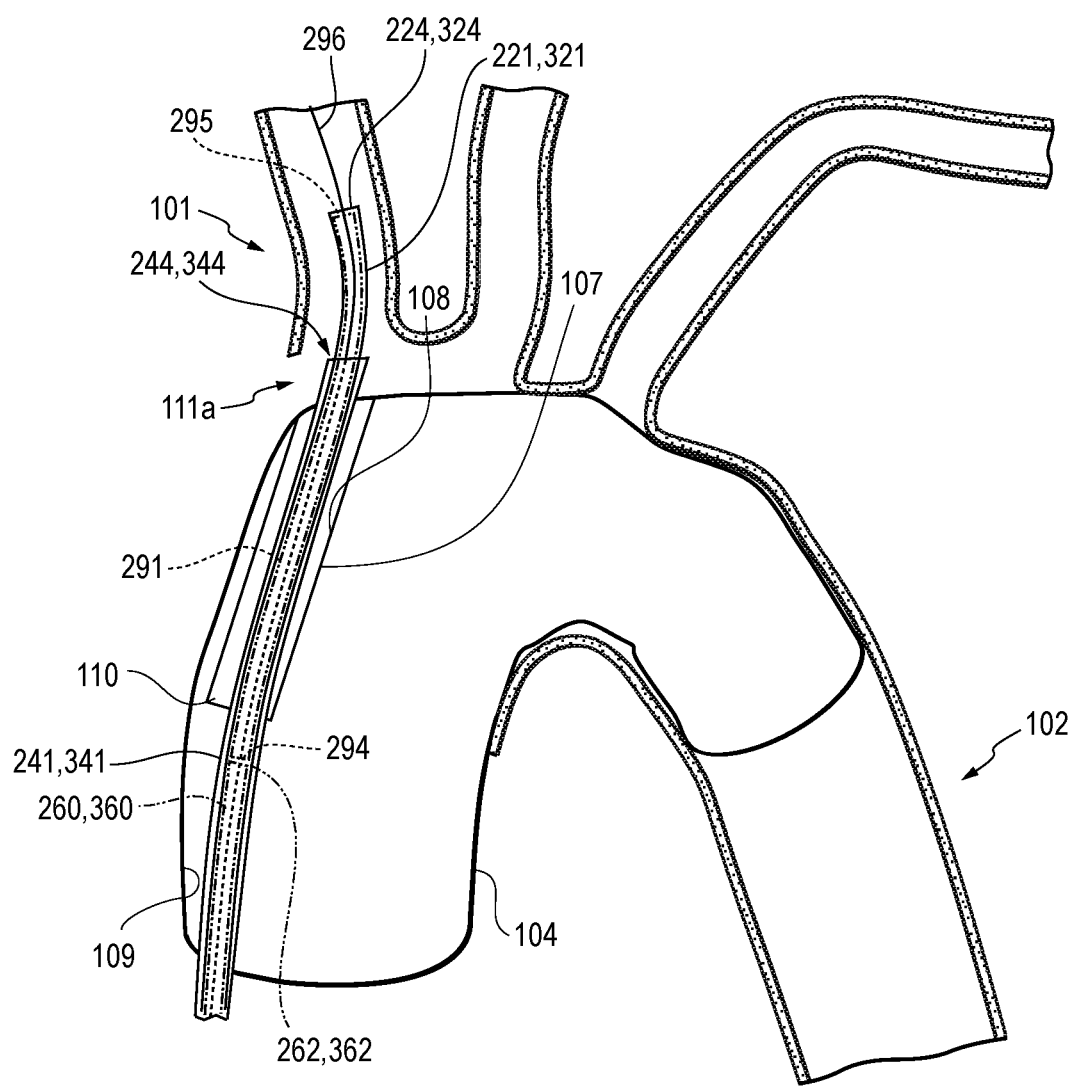

In FIG. 14C, secondary sheath distal end 244, 344 remains disposed at or adjacent to ostium 111a of brachiocephalic artery 105a. Primary sheath 221, 321 includes connection prosthesis 291 within primary sheath lumen 225, 325 in the contracted delivery state as discussed above. FIGS. 14A-14G, 18A, and 18B omit cannula 292 and tip 293 for clarity. Connection prosthesis distal end 295 is adjacent to or longitudinally coincident with primary sheath distal end 224, 324. Connection prosthesis proximal end 294 is adjacent to or abutting pusher distal end 262, 362. For the purposes of the present disclosure, two points, surfaces, structures, etc., may be considered to be longitudinally coincident with each other if the longitudinal offset between them is within a range of tolerance of being precisely longitudinally coincident, where the range of tolerance is less than or equal to 2 millimeters. An acceptable range of tolerance may be less than 2 millimeters depending upon the given clinical application's allowable longitudinal offset between the proximal edge of the placed prosthesis and the proximal edge of the receiving structure. As illustrated in FIGS. 14C-14F, 18A, and 18B, the length of connection prosthesis 291 is calibrated to proximally terminate at inner branch proximal end 110, such that when the preselected overlap is established, connection prosthesis proximal end 294 is at a position longitudinally coincident with inner branch proximal end 110. In some embodiments, connection prosthesis 291 is calibrated so that when the preselected overlap has been established, connection prosthesis proximal end 294 is precisely longitudinally coincident with (i.e., has no longitudinal offset from) inner branch proximal end 110.

In the state depicted in FIG. 14C, primary sheath 221, 321 has been inserted over guidewire 296, with guidewire 296 received in the cannula lumen of cannula 292. Primary sheath 221, 321 has been longitudinally translated through secondary sheath lumen 245, 345, until an indicator of length reference mechanism 280, 380 indicates to the clinician that a sufficient length of primary sheath 221, 321 is received in the lumen of brachiocephalic artery 105a (i.e., the exemplary landing vessel) to provide a preselected overlap of connection prosthesis 291 with brachiocephalic artery 105a.

Using delivery system 200, the indication is provided when primary valve assembly distal end 227 contacts secondary valve assembly proximal end 246, as illustrated for example in FIG. 8. This configuration indicates establishment of the preselected overlap of connection prosthesis 291 with the landing vessel, where the components of delivery system 200 are dimensioned to provide that preselected overlap. Moreover, because the indication is provided via portions of delivery system 200 that are visible in an unaided manner to the clinician, the surgeon is able to know the length of prosthesis in the landing vessel despite the unavailability of fluoroscopy or other imaging modalities to visualize the prosthesis or landing vessel.

Figure 13:
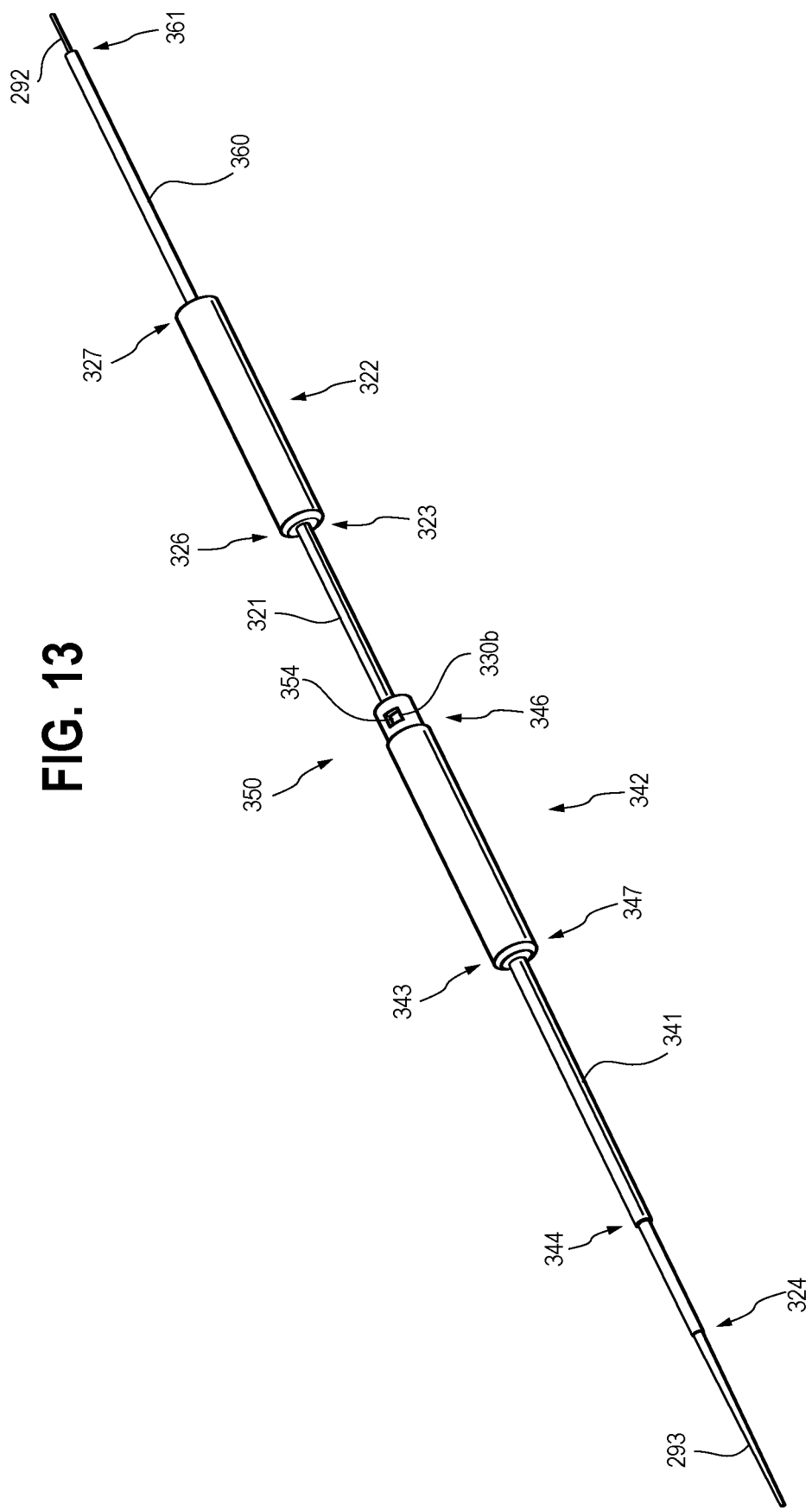
FIG. 13 is a perspective view of the delivery system of FIG. 9 in a second state indicating that a preselected overlap has been established.

Using delivery system 300, the indication is provided when an indicia corresponding to the desired preselected overlap of connection prosthesis 291 with brachiocephalic artery 105a is visible through indicator window 354, as illustrated for example in FIG. 13, which depicts indicia 330b aligned with and visible through indicator window 354. This exemplary configuration indicates establishment of a 90 millimeter overlap of connection prosthesis 291 with the landing vessel. Moreover, because the indication is provided via portions of delivery system 300 that are visible in an unaided manner to the clinician, the surgeon is able to know the length of prosthesis in the landing vessel despite the unavailability of fluoroscopy or other imaging modalities to visualize the prosthesis or landing vessel.

Additionally, because the components of delivery system 200, 300 which enter main body prosthesis 104, inner branch 107, and the landing vessel (e.g., brachiocephalic artery 105a) are flexible, they are able to track through main body prosthesis 104, inner branch 107, and the landing vessel in a desirable manner.

Figure 14D:
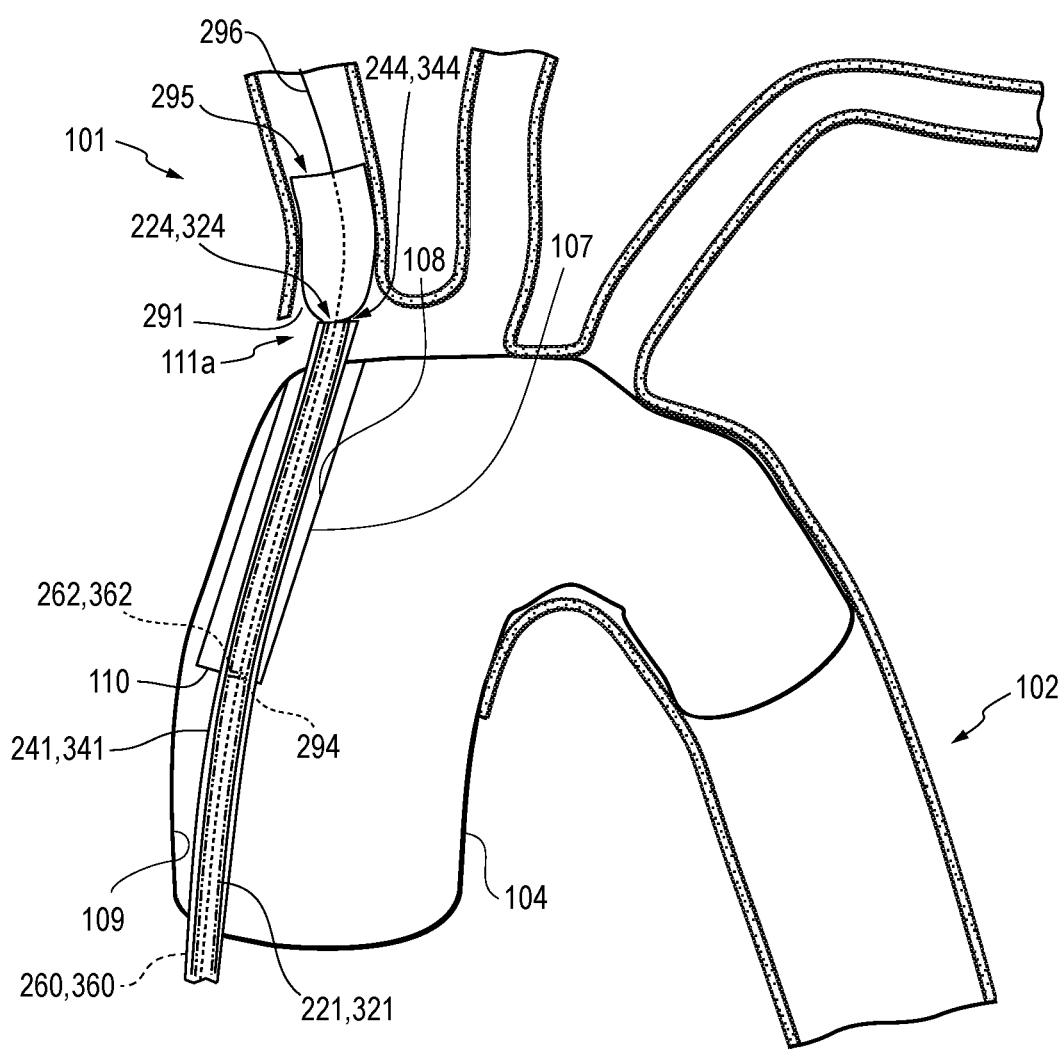

In FIG. 14D, the clinician begins to deploy connection prosthesis 291, by longitudinally translating or retracting primary sheath 221, 321 proximally relative to pusher 260, 360, connection prosthesis 291, and secondary sheath assembly 240, 340. For example, the clinician may pull back on primary valve assembly 222, 322, while maintaining secondary sheath assembly 240, 340 and pusher 260, 360 at their respective positions. Primary sheath distal end 224, 324 is now longitudinally coincident with secondary sheath distal end 244, 344. Connection prosthesis 291 is thus partially exposed and begins to expand within brachiocephalic artery 105a, maintaining the preselected overlap of connection prosthesis 291 with brachiocephalic artery 105a.

Figure 14E:
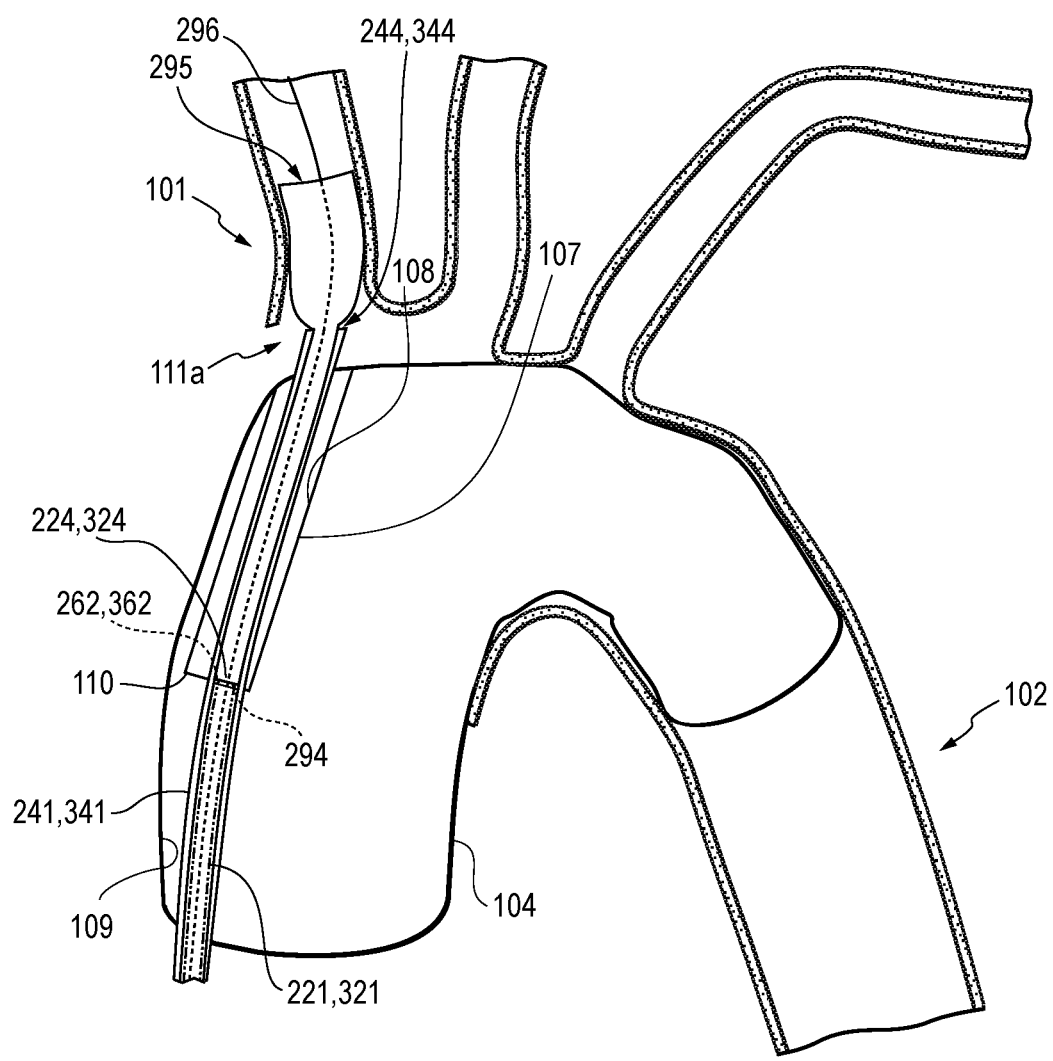

In FIG. 14E, the clinician has continued to longitudinally translate or retract primary sheath 221, 321 proximally until primary sheath distal end 224, 324 is proximal to inner branch proximal end 110, allowing the portion of connection prosthesis 291 proximal to secondary sheath distal end 244, 344 to expand within secondary sheath lumen 245, 345. For example, the clinician may continue pulling back on primary valve assembly 222, 322, while maintaining secondary sheath assembly 240, 340 and pusher 260, 360 at their respective positions. Connection prosthesis 291 continues to maintain its preselected overlap with brachiocephalic artery 105a, and connection prosthesis proximal end 294 continues to be longitudinally coincident with proximal edge 110 of inner branch 107.

Figure 14F:
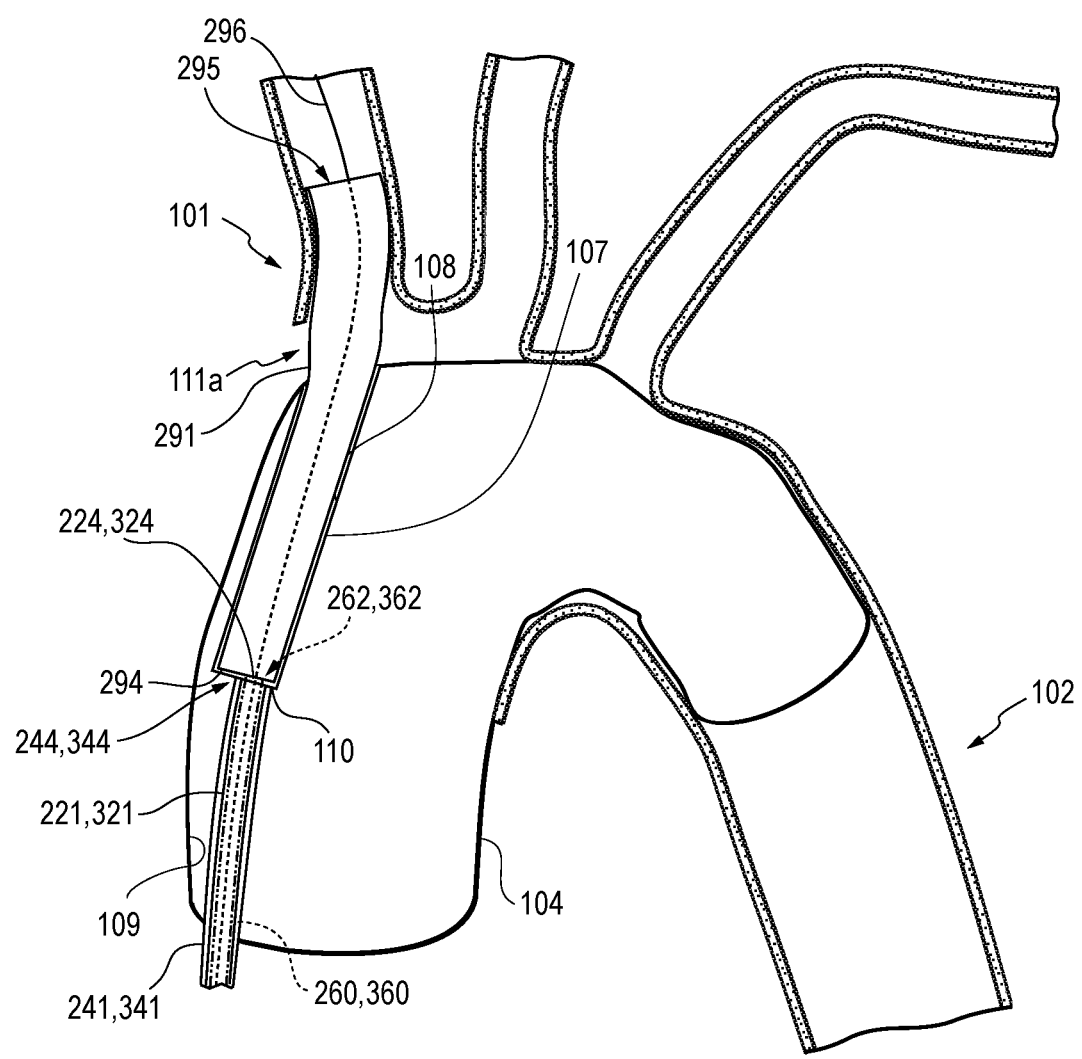
Figure 14G:
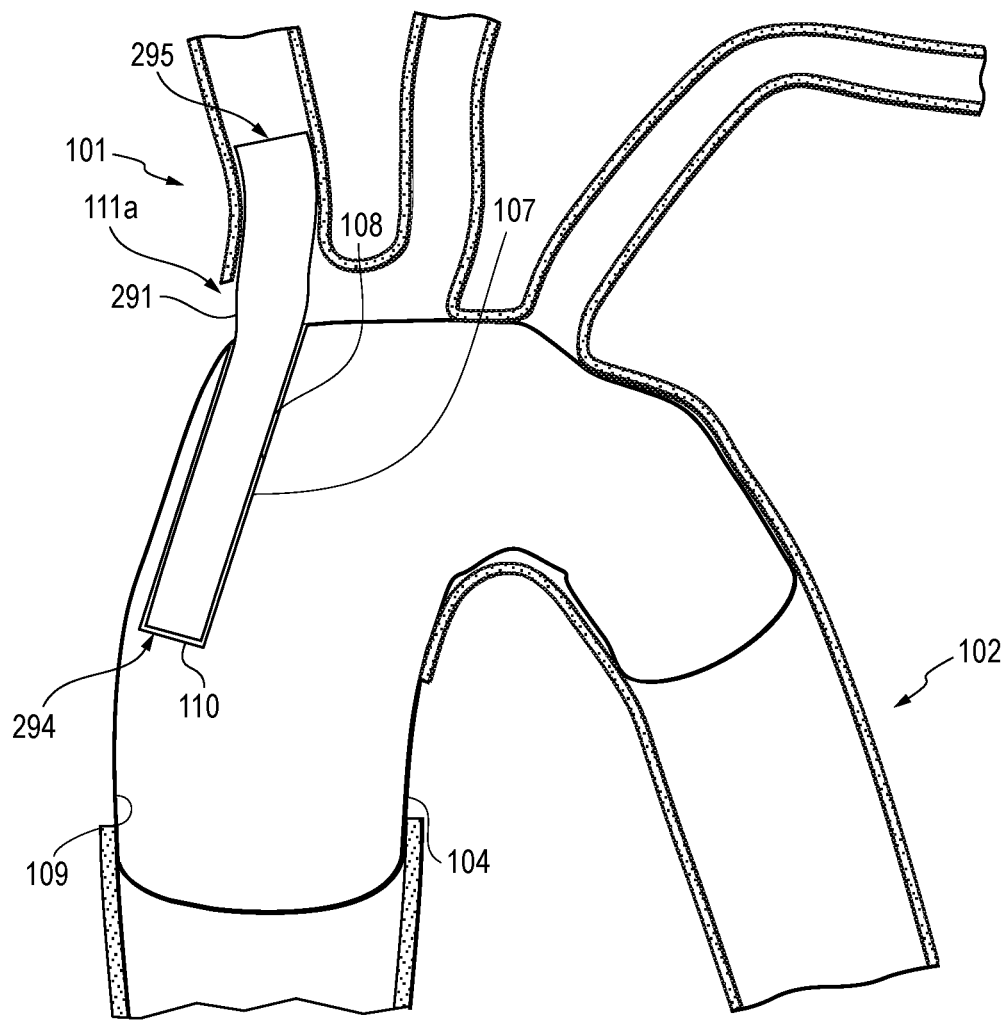

In FIG. 14F, the clinician has longitudinally translated or retracted secondary sheath 221, 321 proximally relative to inner branch 107, pusher 260, 360, connection prosthesis 291, and primary sheath 221, 321, allowing connection prosthesis 291 to fully expand within brachiocephalic artery 105a and within receiving lumen 108 of inner branch 107. Connection prosthesis 291 continues to maintain its preselected overlap with brachiocephalic artery 105a, and connection prosthesis proximal end 294 continues to be longitudinally coincident with proximal edge 110 of inner branch 107.

In some embodiments, similar steps would then be performed to connect left common carotid artery 105b and left subclavian artery 105c with their corresponding branches (not shown). Then, in FIG. 14G, delivery system 200, 300 and guidewire 296 are withdrawn from main body prosthesis 104, and aortic root 103 is connected to main body prosthesis 104.

FIGS. 14D-14F thus illustrate methods in which primary sheath 221, 321 is retracted first, deploying connection prosthesis 291 partially into secondary sheath 241, 341, and in which secondary sheath 241, 341 is then retracted second, fully deploying connection prosthesis 291 within brachiocephalic artery 105*a* and inner branch 107. However, other methods of deployment are discussed below.

FIGS. 15A, 15B, 16A, 16B, 17A, 17B, 18A, 18B illustrate structures and methods that lock primary sheath assembly 220, 320 and secondary sheath assembly 240, 340 together for deployment of connection prosthesis 291 such that longitudinal translation or retraction of primary sheath assembly 220, 320 in the proximal direction causes longitudinal translation or retraction of secondary sheath assembly 240, 340 in the proximal direction. Embodiments where primary sheath assembly 220, 320 and secondary sheath 240, 340 are locked together in this manner provide the benefit that connection prosthesis 291 can be deployed directly into brachiocephalic artery 105*a* and inner branch 107 with a single retraction motion.

In methods where primary sheath assembly 220, 320 and secondary sheath 240, 340 are locked together for deployment of connection prosthesis 291, the steps may, until delivery system 200, 300 is arranged as illustrated in FIG. 14C, be identical to the steps described above in connection with FIGS. 14A-14C. Moreover, primary sheath assembly 220, 320 and secondary sheath 240, 340 may, until delivery system 200, 300 is arranged as illustrated in FIG. 14C, be able to longitudinally translate relative to each other. However, instead of separately retracting primary sheath 221, 321 in the manner described above in connection with FIGS. 14D-14F, when delivery system 200, 300 is arranged as illustrated in FIG. 14C, primary sheath assembly 220, 320 and secondary sheath 240, 340 are then locked together in a suitable manner, examples of which are described below in connection with FIGS. 15A, 15B, 16A, 16B, 17A, and 17B.

Figure 15A:
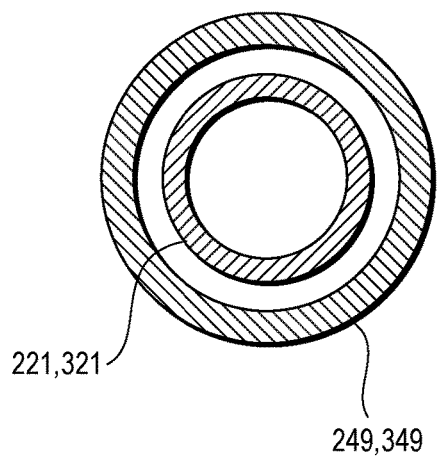
FIG. 15A is a transverse cross-sectional view illustrating a primary sheath assembly of the delivery system of FIG. 3 or FIG. 9 in a valve of a secondary sheath assembly of the delivery system of FIG. 3 or FIG. 9, where the valve is in an open state.
Figure 15B:
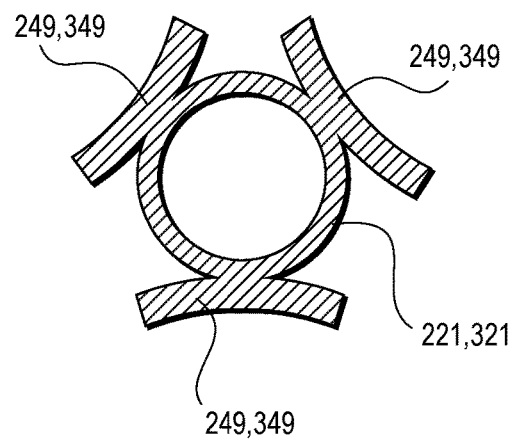
FIG. 15B is a transverse cross-sectional view illustrating the primary sheath of FIG. 15A in the valve of FIG. 15A, where the valve is in a closed state.

One manner of locking primary sheath assembly 220, 320 and secondary sheath assembly 240, 340 together is illustrated in FIGS. 15A and 15B. FIG. 15A depicts delivery system 200, 300 in the arrangement illustrated in FIG. 14C. FIG. 15B illustrates the clinician having then closed secondary valve 249, 349 around primary sheath 221, 321, with the resulting pressure on primary sheath 221, 321 locking primary sheath assembly 220, 320 and secondary sheath 240, 340 together with respect to relative longitudinal translation.

Figure 16A:
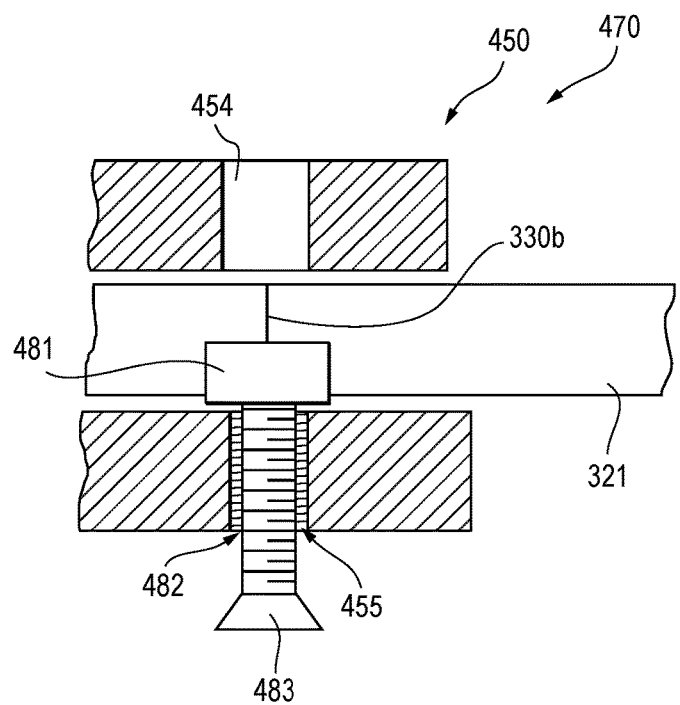
FIG. 16A is a partial longitudinal cross-sectional view illustrating a first sheath-locking mechanism locking a primary sheath assembly of the delivery system of FIG. 9 together with a secondary sheath assembly of the delivery system of FIG. 9.
Figure 16B:
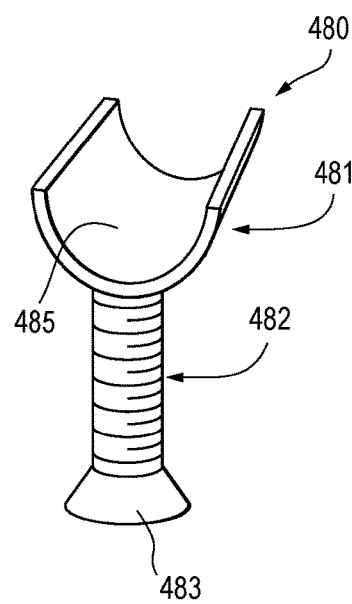
FIG. 16B is an isolated perspective view illustrating a pressure application assembly of the sheath locking mechanism of FIG. 16A.

A second manner of locking primary sheath assembly 220, 320 and secondary sheath assembly 240, 340 together is illustrated in FIGS. 16A and 16B, which illustrate exemplary sheath-locking mechanism 470. Sheath-locking mechanism 470 includes indicator window assembly 450 and pressure application assembly 480. Indicator window assembly 450 is generally similar in terms of structure and function to indicator window assembly 350. Indicator window assembly 450 may for example replace indicator window assembly 350 on secondary valve assembly 342. Indicator window assembly 450 includes indicator window 454, which is generally similar in terms of structure and function to indicator window 354. Indicator window assembly 450 further comprises internally threaded hole 455 passing through a bottom wall of indicator window assembly 450.

Pressure application assembly 480 includes sleeve 481, set screw 482, and grip 483. Sleeve 481 is an extended generally arcuate structure comprising inner channel 485. Inner channel 485 is shaped and dimensioned to conform to an outer surface of primary sheath 321. Sleeve 481 is disposed between the outer surface of primary sheath 321 and internally threaded hole 455. Sleeve 481 is connected with set screw 482 at a top of set screw 482. Set screw 482 passes through internally threaded hole 455 and includes external threads that correspond with the internal threads of internally threaded hole 455.

When an indicia on primary sheath 321 that indicates establishment of a desired preselected overlap (e.g., indicia 330*b*) is aligned with and visible through indicator window 454, the clinician may lock primary sheath assembly 320 and secondary sheath assembly 340 together by using grip 483 to turn set screw 482, thereby pressing sleeve 481 radially inward into primary sheath 321. The generated pressure locks primary sheath assembly 320 and secondary sheath assembly 340 together with respect to relative longitudinal translation.

Figure 17A:
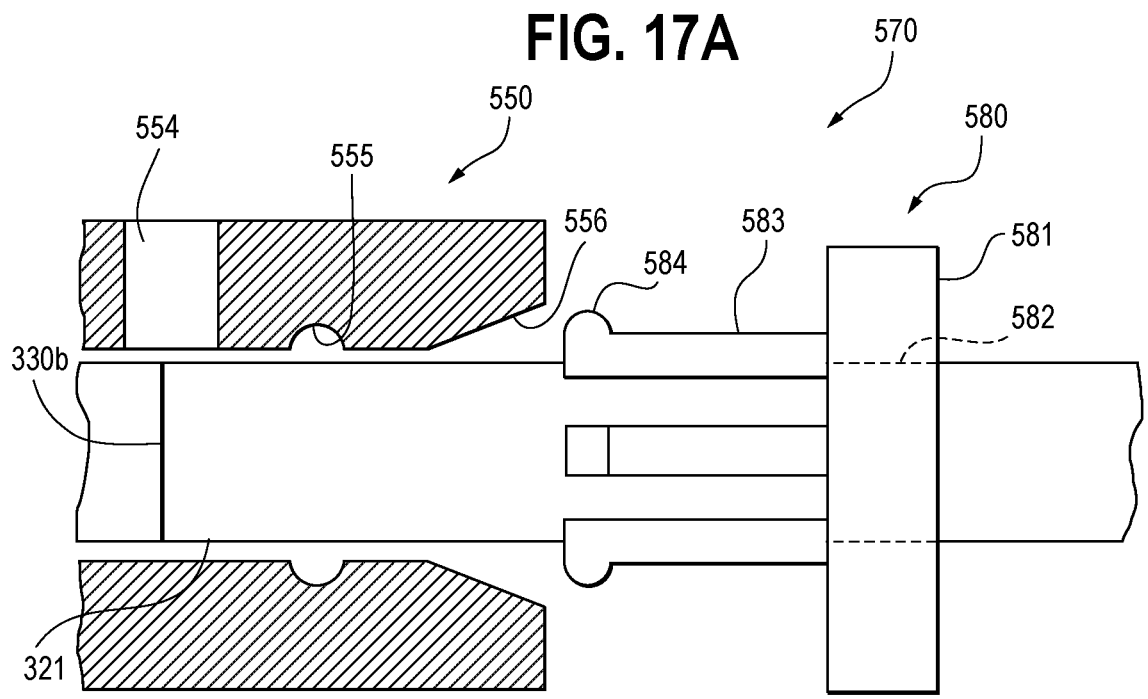
FIG. 17A is a partial longitudinal cross-sectional view illustrating a second sheath-locking mechanism in a state prior to locking a primary sheath assembly of the delivery system of FIG. 9 together with a secondary sheath assembly of the delivery system of FIG. 9.
Figure 17B:
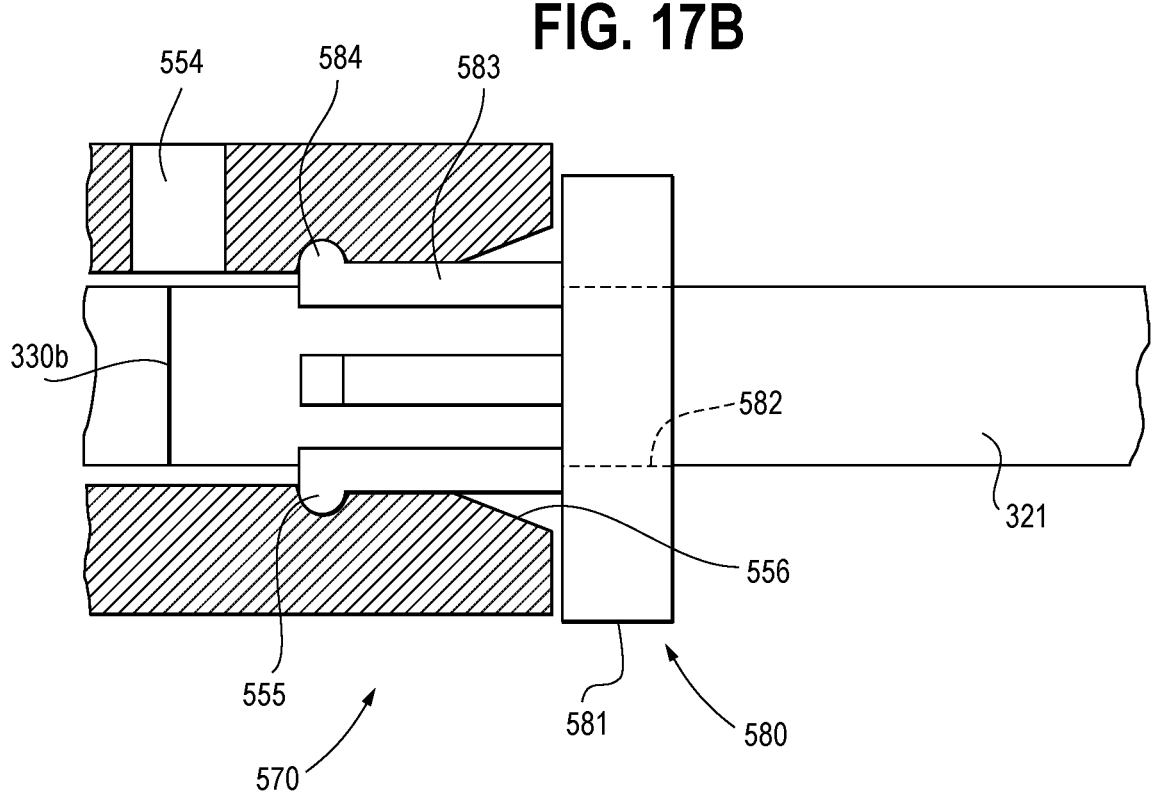
FIG. 17B is a partial longitudinal cross-sectional view illustrating the sheath-locking mechanism of FIG. 17A in a state where the primary sheath assembly of the delivery system of FIG. 9 has been locked together with the secondary sheath assembly of the delivery system of FIG. 9.

A third manner of locking primary sheath assembly 220, 320 and secondary sheath assembly 240, 340 together is illustrated in FIGS. 17A and 17B, which illustrate exemplary sheath locking mechanism 570. Sheath-locking mechanism 570 includes indicator window assembly 550 and collet button 580. Indicator window assembly 550 is generally similar in terms of structure and function to indicator window assembly 350. Indicator window assembly 550 may for example replace indicator window assembly 350 on secondary valve assembly 342. Indicator window assembly 550 includes indicator window 554 and indicator window assembly lumen 553, and which are generally similar in terms of structure and function to indicator window 354 and indicator window assembly lumen 353. Indicator window assembly 550 further comprises slot 555 facing into indicator window assembly lumen 553. Slot 555 may be a continuous slot extending within and circumferentially around the inner surface of indicator window assembly 550. Indicator window assembly 550 further comprises circumferential taper 556 generally facing into indicator window assembly lumen 553. Circumferential taper 556 is at its widest at indicator window assembly proximal end 557 and narrows distally of indicator window assembly proximal end 557.

Collet button 580 includes collet body 581, which may be a generally annular structure, and comprises collet lumen 582 therethrough. Collet lumen 582 receives primary sheath 321 longitudinally therethrough such that collet button 580 can longitudinally translate on and along primary sheath 321. Collet button 580 further includes a plurality of flexible teeth 583 connected to and extending distally from a distal end of collet body 581. The plurality of flexible teeth 583 are disposed circumferentially around collet lumen 582. For example, plurality of flexible teeth 583 may include four teeth symmetrically disposed circumferentially around collet lumen 582. Each of the plurality of flexible teeth 583 may include a respective radial protrusion 584 at the tooth's distal end. Each radial protrusion is shaped and dimensioned to conform to slot 555.

When an indicia on primary sheath 321 that indicates establishment of a desired preselected overlap (e.g., indicia 330*b*) is aligned with and visible through indicator window 554, the clinician may lock primary sheath assembly 320 and secondary sheath assembly 340 together by longitudinally translating collet button 580 distally along primary sheath 321 and towards indicator window assembly 550. As collet button 580 advances in this manner, the plurality of flexible teeth slide along circumferential taper 556, causing each of the plurality of flexible teeth 583 to bend radially inward until its respective radial protrusion 584 engages with slot 555, thereby applying pressure to the outer surface of primary sheath 321 and locking primary sheath assembly 320 and secondary sheath assembly 340 together with respect to relative longitudinal translation.

Figure 18A:
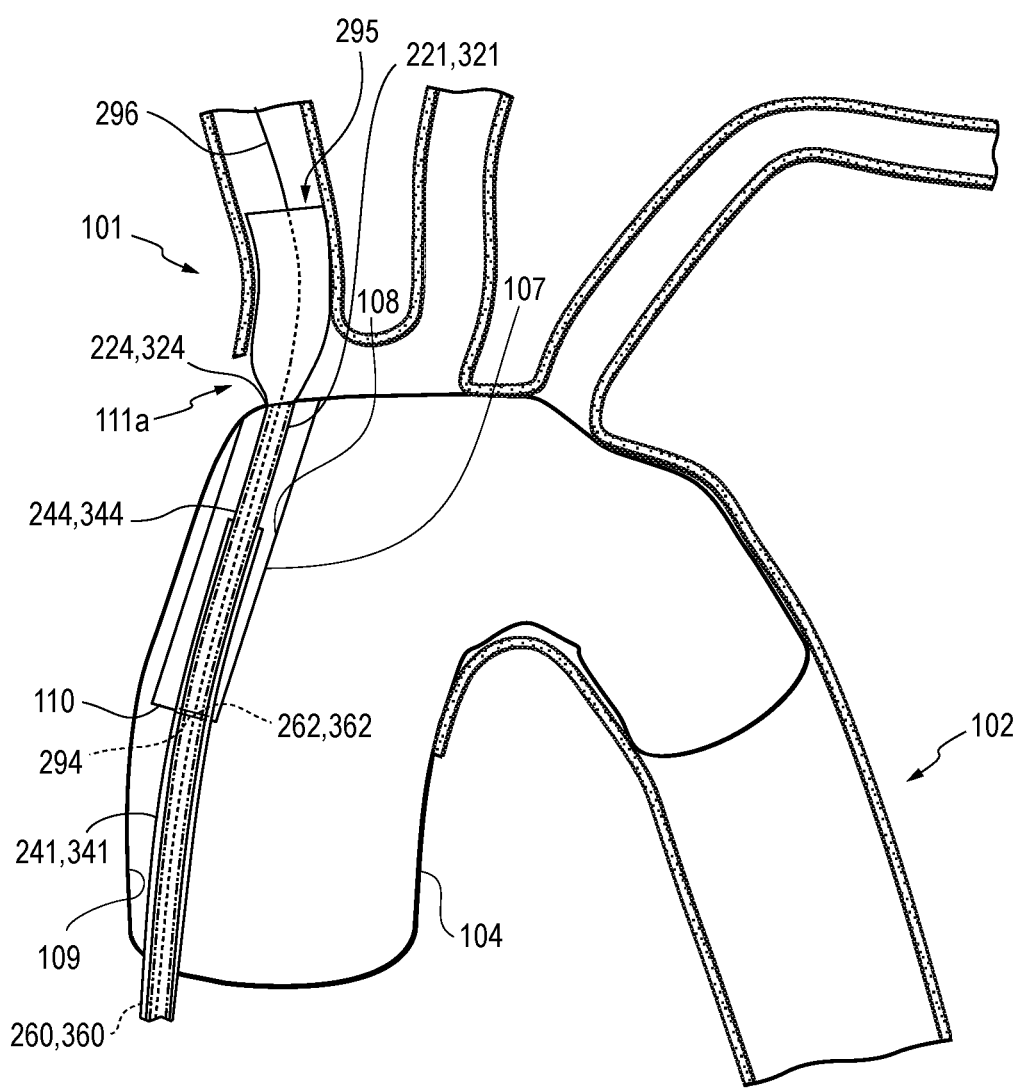
FIG. 18A is partial cross-sectional view illustrating an alternative method of deploying the connection prosthesis of the delivery system of FIG. 3 or FIG. 9 from the state depicted in FIG. 14C, when the primary sheath assembly of the delivery system of FIG. 3
Figure 18B:
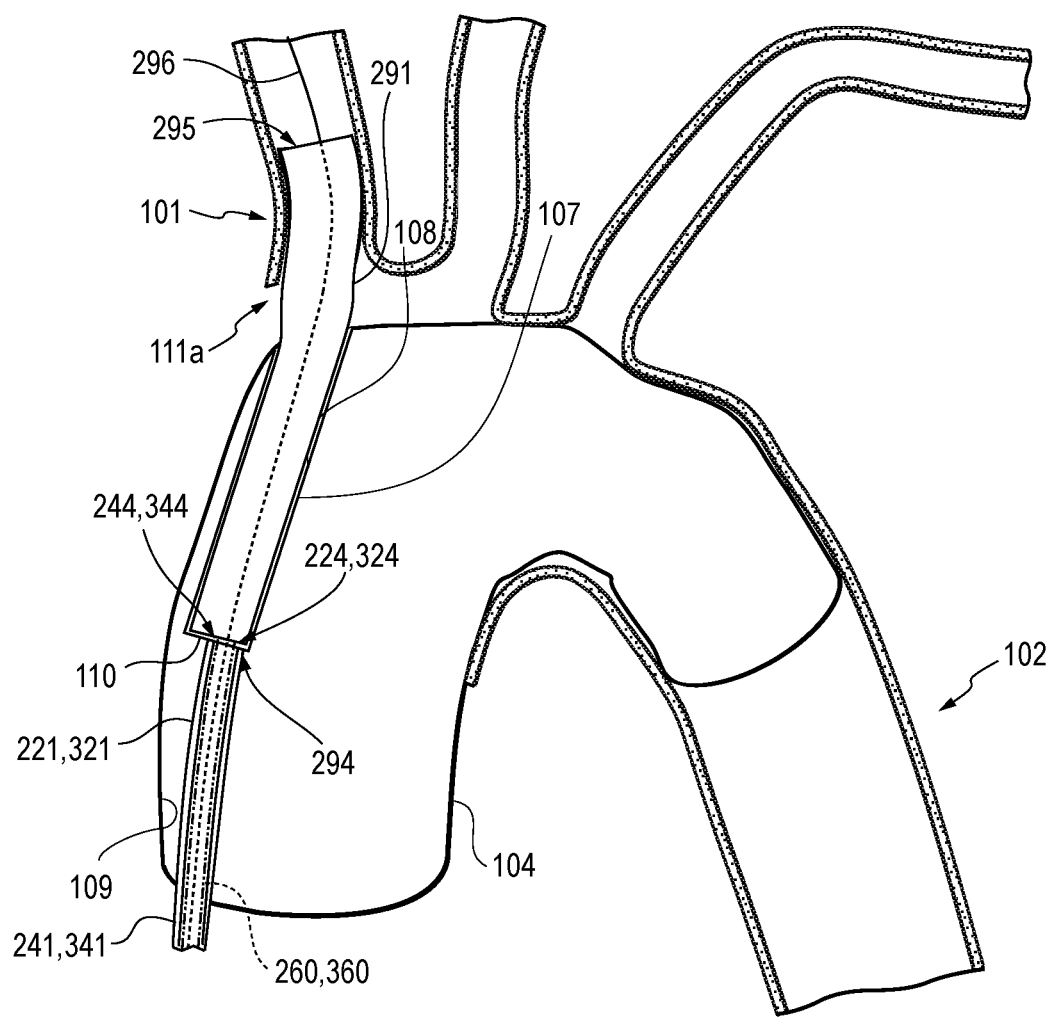
FIG. 18B is a partial cross-sectional view of the method of FIG. 18A illustrating the primary sheath assembly of the delivery system of FIG. 3 or FIG. 9 locked together with and simultaneously retracted with the secondary sheath assembly of the delivery system of FIG. 3 or FIG. 9 until the connection prosthesis is fully expanded in the landing vessel and inner branch.

Once primary sheath assembly 220, 320 and secondary sheath assembly 240, 340 are locked together with respect to relative longitudinal translation, whether in any of the above manners or in any other suitable manner, deployment of connection prosthesis 291 may proceed. FIGS. 18A and 18B depict steps of deploying connection prosthesis 291 when primary sheath assembly 220, 320 and secondary sheath assembly 240, 340 are locked together with respect to relative longitudinal translation, which may be an alternative to the steps described above in connection with FIGS. 14D-14F.

In FIG. 18A, the clinician has begun longitudinally translating or retracting primary sheath 221, 321 proximally relative to inner branch 107, connection prosthesis 291, and pusher 260, 360, for example by pulling on primary valve assembly 222, 322 while maintaining pusher 260, 360 at its current position. Accordingly, primary sheath distal end 224, 324 is positioned proximal to ostium 111a of brachiocephalic artery 105a. Connection prosthesis 291 is thus partially exposed and begins to expand within brachiocephalic artery 105a, maintaining the preselected overlap of connection prosthesis 291 with brachiocephalic artery 105a. With primary sheath assembly 220, 320 locked together with secondary sheath assembly 240, 340 as discussed above, retracting primary sheath 221, 321 in this manner causes simultaneous retraction of secondary sheath 241, 341, such that secondary sheath distal end 244, 344 is positioned within inner branch lumen 108.

In FIG. 18B, the clinician has continued to longitudinally translate or retract primary sheath 221, 321 proximally until primary sheath distal end 224, 324 is proximal to inner branch proximal end 110. With primary sheath assembly 220, 320 locked together with secondary sheath assembly 240, 340 as discussed above, retracting primary sheath 221, 321 in this manner causes simultaneous retraction of secondary sheath 241, 341, which allows connection prosthesis 291 to fully expand directly within brachiocephalic artery 105a and within receiving lumen 108 of inner branch 107. Connection prosthesis 291 continues to maintain its preselected overlap with brachiocephalic artery 105a, and connection prosthesis proximal end 294 continues to be longitudinally coincident with proximal edge 110 of inner branch 107. Then, the method may continue in the manner described above in connection with FIG. 14G.

Figure 19A:
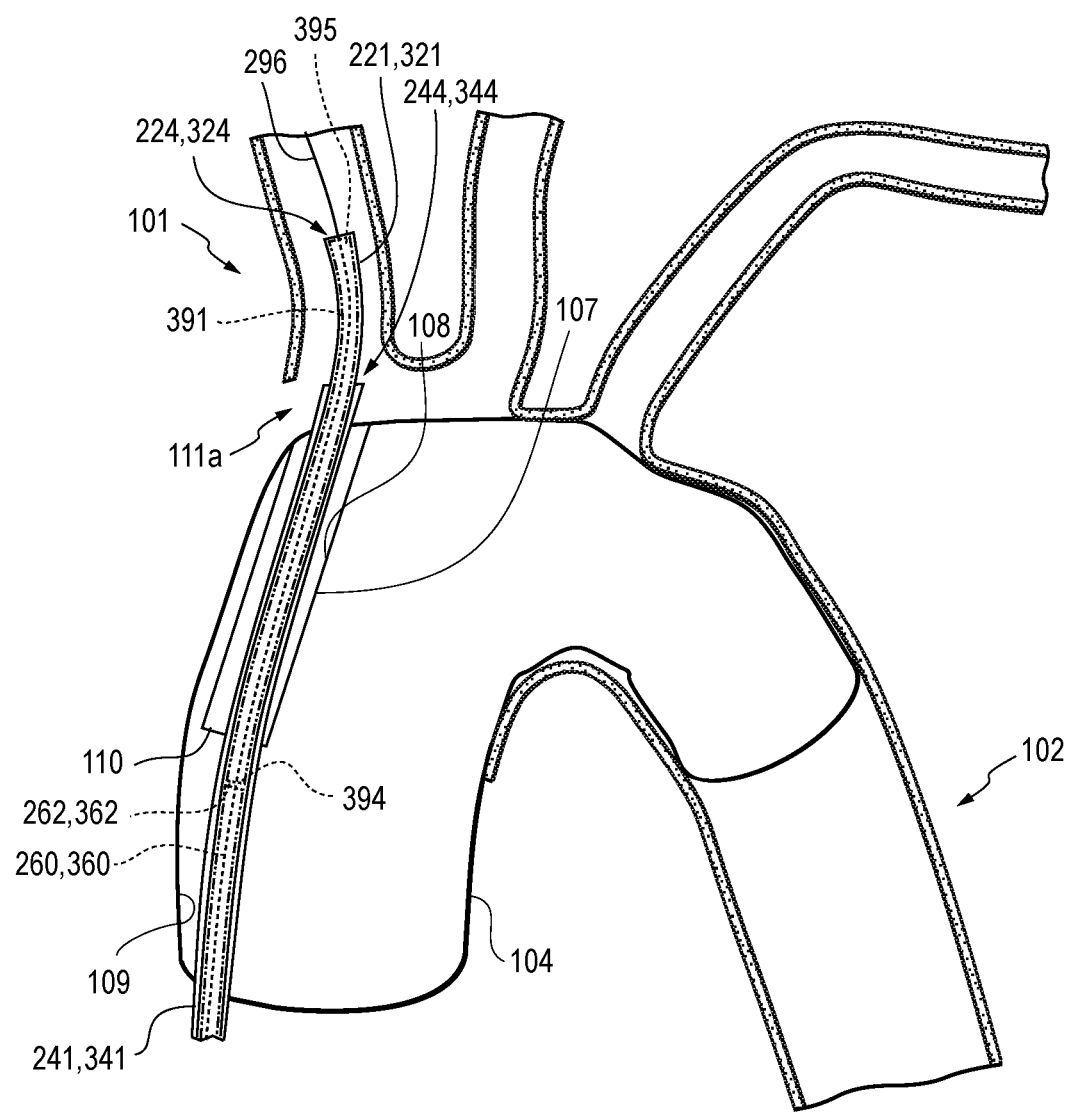
FIG. 19A is a partial cross-sectional view of a partially completed frozen elephant trunk procedure illustrating placement.
Figure 19B:
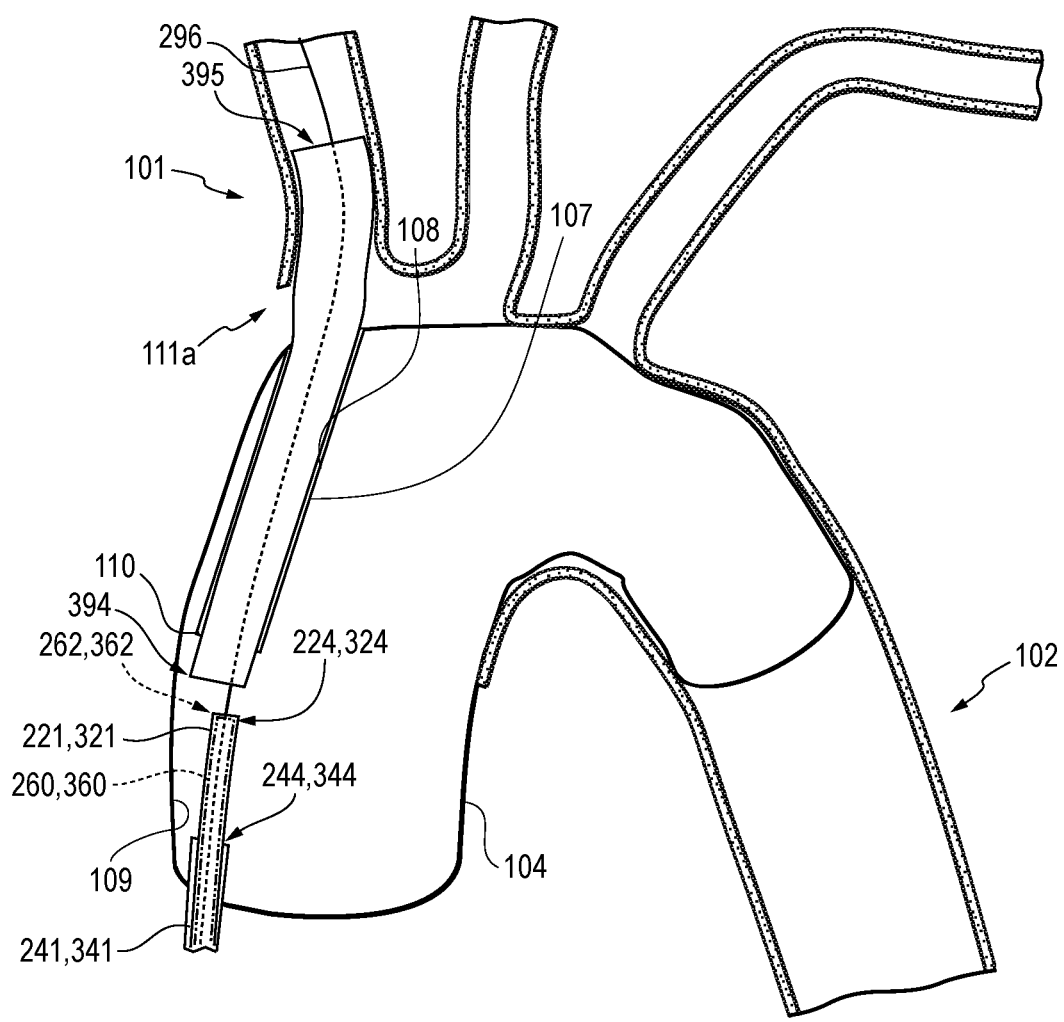
FIG. 19B is a partial cross-sectional view of the partially completed frozen elephant trunk procedure of FIG. 19A illustrating the primary sheath assembly and secondary sheath assembly having been simultaneously retracted until the connection prosthesis is fully expanded in the landing vessel and inner branch.
Figure 19C:
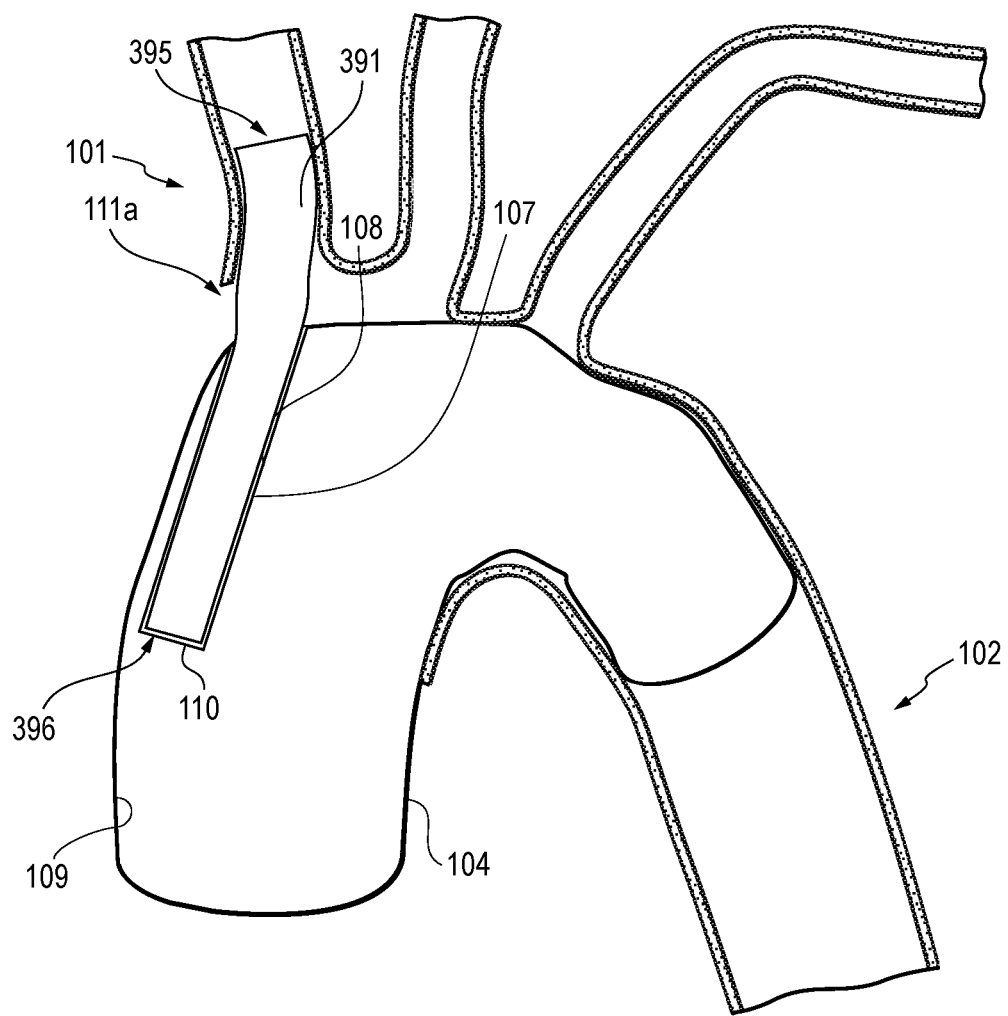
FIG. 19C is a partial cross-sectional view of the partially completed frozen elephant trunk procedure of FIG. 19A illustrating the connection prosthesis having been tailored to be flush with the inner branch proximal end.

FIGS. 14A-14G, 18A, and 18B illustrate methods of placing connection prosthesis 291, which has a length calibrated to terminate at internal branch proximal end 110. However, the present disclosure also contemplates methods of placing a connection prosthesis that is manufactured to extend proximally out of the internal branch when the preselected overlap with the landing vessel has been established. The clinician may then tailor the placed connection prosthesis so that its proximal end is longitudinally coincident with the proximal end of the internal branch. For example, FIGS. 19A-19C illustrate steps of a method in which primary sheath 221, 321 includes connection prosthesis 391 rather than connection prosthesis 291. Connection prosthesis 391 is longer than connection prosthesis 291, but is otherwise similar to connection prosthesis 291, and includes connection prosthesis proximal end 394 and connection prosthesis distal end 395. FIGS. 19A-19C omit a cannula and tip from connection prosthesis assembly 391 for clarity.

FIG. 19A illustrates a state of primary sheath assembly 220, 320 and secondary sheath 240, 340 that is generally the same as the state depicted in FIG. 14C, with a few exceptions. First, primary sheath 221, 321 instead includes longer connection prosthesis 391 within primary sheath lumen 225, 325 in the contracted delivery state. Accordingly, with primary sheath distal end 224, 324 positioned in the depicted manner establishing the preselected overlap of connection prosthesis 391 with inner branch 107, connection prosthesis proximal end 394 is positioned proximally to inner branch proximal end 110. Second, because connection prosthesis 391 is longer than connection prosthesis 291, pusher 260, 360 is disposed more proximally within primary sheath 221, 321 than it does when primary sheath 221, 321 includes connection prosthesis 291.

In FIG. 19B, the clinician has longitudinally translated or retracted primary sheath 221, 321 proximally until primary sheath distal end 224, 324 is proximal to inner branch proximal end 110. With primary sheath assembly 220, 320 locked together with secondary sheath assembly 240, 340 as discussed above in connection with FIGS. 15A, 15B, 16A, 16B, 17A, 17B, 18A, and 18B, retracting primary sheath 221, 321 in this manner has caused simultaneous retraction of secondary sheath 241, 341, which allows connection prosthesis 391 to fully expand directly within brachiocephalic artery 105a and within receiving lumen 108 of inner branch 107. Connection prosthesis 391 continues to maintain its preselected overlap with brachiocephalic artery 105a, and connection prosthesis proximal end 394 continues to be positioned proximally to proximal edge 110 of inner branch 107.

Although FIGS. 19A and 19B illustrate a deployment of connection prosthesis 391 in which primary sheath assembly 220, 320 is locked together with secondary sheath assembly 240, 340, and which would proceed in a manner similar to the steps described above in connection with FIGS. 18A, and 18B, this disclosure also includes deploying connection prosthesis 391 from the state illustrated in FIG. 19A in a manner similar to that described above in connection with FIGS. 14D-14F, i.e., with primary sheath 221, 321 being retracted first, deploying connection prosthesis 391 partially into secondary sheath 241, 341, with secondary sheath 241, 341 then being retracted second, fully deploying connection prosthesis 391 within brachiocephalic artery 105a and inner branch 107, but with connection prosthesis 391 maintaining its preselected overlap with brachiocephalic artery 105a, and connection prosthesis proximal end 394 continuing to be positioned proximally to proximal edge 110 of inner branch 107.

Regardless of whether connection prosthesis 391 is deployed using a single retraction of primary sheath assembly 220, 320 and secondary sheath assembly 240, 340 or by first retracting primary sheath assembly 220, 320 and then retracting secondary sheath assembly 240, 340, once connection prosthesis 391 is in the state depicted in FIG. 19B, the clinician may then, in any suitable manner, tailor connection prosthesis 391 to have a new connection prosthesis proximal end 396 that is flush with, or longitudinally coincident with, proximal edge 110 of inner branch 107, as illustrated for example in FIG. 19C, for example by trimming or cutting connection prosthesis 391 at proximal edge 110. Then, the method may continue in the manner described above in connection with FIG. 14G.

Although specific examples in the instant disclosure have generally focused on an open cardiothoracic surgical procedure, such as a frozen elephant trunk procedure, those of skill in the art may recognize that aspects of the instant disclosure may be applicable to placing connection prostheses during endovascular procedures. Additionally, those skilled in the art may recognize that aspects of the instant disclosure may be applicable to placing types of prostheses other than connection prostheses, and to placing other types of medical implants.

While various embodiments of the invention have been described, the invention is not to be restricted except in light of the attached claims and their equivalents. Moreover, the advantages described herein are not necessarily the only advantages of the invention and it is not necessarily expected that every embodiment of the invention will achieve all of the advantages described.

We claim:

1. A delivery system comprising:
    a primary sheath extending from a primary sheath distal end to a primary sheath proximal end and comprising a primary sheath lumen from the primary sheath distal end to the primary sheath proximal end;
    a secondary sheath extending from a secondary sheath distal end to a secondary sheath proximal end and comprising a secondary sheath lumen from the secondary sheath distal end to the secondary sheath proximal end, the primary sheath at least partially received within the secondary sheath lumen such that the primary sheath translates longitudinally within the secondary sheath lumen;
    a prosthesis having proximal and distal ends and being received within the primary sheath lumen adjacent to the primary sheath distal end in a contracted delivery state; and
    a length reference section disposed at the secondary sheath proximal end, wherein the length reference section indicates a preselected length of the primary sheath distal end that extends distally out of the secondary sheath distal end during the contracted delivery state of the prosthesis.

2. The delivery system of claim 1, wherein the length reference section comprises an indicator window assembly disposed at the secondary sheath proximal end, the indicator window assembly comprising an indicator window assembly proximal end and an indicator window assembly distal end and comprising an indicator window assembly lumen from the indicator window assembly proximal end to the indicator window assembly distal end, the indicator window assembly lumen at least partially receiving the primary sheath.

3. The delivery system of claim 2, wherein the indicator window assembly comprises an indicator window through which an outer surface of the primary sheath is observable.

4. The delivery system of claim 3, wherein the length reference section further comprises at least one indicia disposed at the outer surface of the primary sheath at a position calibrated such that when the indicia is longitudinally aligned with and observable through the indicator window, the length of the primary sheath distal end that extends distally out of the secondary sheath distal end during the contracted delivery state of the prosthesis is indicated.

5. The delivery system of claim 4, wherein the length of the primary sheath distal end that extends distally out of the secondary sheath distal end during the contracted delivery state indicates a length of the prosthesis that extends distally out of the secondary sheath distal end during the contracted delivery state.

6. The delivery system of claim 3, wherein the length reference section further comprises a plurality of indicia disposed at the outer surface of the primary sheath, each indicia of the plurality of indicia being longitudinally spaced apart from each other indicia of the plurality of indicia, wherein each of the plurality of indicia becomes observable through the indicator window as the primary sheath longitudinally translates through the indicator window assembly lumen.

7. The delivery system of claim 6, wherein each indicia of the plurality of indicia is disposed at a respective position calibrated such that when the indicia is longitudinally aligned with and observable through the indicator window, the length of the primary sheath distal end that extends distally out of the secondary sheath distal end during the contracted delivery state of the prosthesis is indicated.

8. The delivery system of claim 1, wherein the primary sheath longitudinally translates proximally relative to the secondary sheath to deploy the prosthesis from the contracted delivery state to an expanded deployed state.

9. A delivery system comprising:
    a primary sheath extending from a primary sheath distal end to a primary sheath proximal end and comprising a primary sheath lumen from the primary sheath distal end to the primary sheath proximal end;
    a secondary sheath extending from a secondary sheath distal end to a secondary sheath proximal end and comprising a secondary sheath lumen from the secondary sheath distal end to the secondary sheath proximal end, the primary sheath at least partially received within the secondary sheath lumen such that the primary sheath translates longitudinally within the secondary sheath lumen, wherein the delivery system has a loaded configuration in which a prosthesis having proximal and distal ends is received within the primary sheath lumen adjacent to the primary sheath distal end in a contracted delivery state;
    a length reference section disposed at the secondary sheath proximal end, wherein the length reference section indicates a preselected length of the primary sheath distal end that extends distally out of the secondary sheath distal end during the contracted delivery state of the prosthesis; and
    a sheath-locking section that selectively locks the primary sheath to the secondary sheath such that longitudinal proximal translation of the primary sheath causes longitudinal proximal translation of the secondary sheath.

10. The delivery system of claim 9, wherein the sheath-locking section comprises a valve assembly disposed at the secondary sheath proximal end, the valve assembly comprising a valve having an open state in which the primary sheath longitudinally translates through the valve and a closed state in which the valve applies pressure to an outer surface of the primary sheath, locking the primary sheath to the secondary sheath.

11. The delivery system of claim 9, wherein the sheath-locking section comprises a pressure application assembly that selectively applies pressure to an outer surface of the primary sheath in a radial direction.

12. The delivery system of claim 11, wherein the pressure application assembly comprises:
    a threaded structure passing through a wall of the secondary sheath; and
    a sleeve that conforms to the outer surface of the primary sheath, the sleeve disposed at a top of the threaded structure,
    wherein turning the threaded structure within the wall of the secondary sheath selectively applies pressure to the outer surface of the primary sheath in the radial direction.

13. The delivery system of claim 12, wherein the length reference section comprises an indicator window assembly comprising an indicator window through which the outer surface of the primary sheath is observable, the threaded structure and the sleeve being longitudinally aligned with the indicator window.

14. The delivery system of claim 9, wherein the sheath-locking section comprises a structure that longitudinally translates on and along the primary sheath between an unlocked state in which the primary sheath longitudinally translates relative to the secondary sheath and a locked state in which the primary sheath is locked to the secondary sheath with respect to longitudinal translation.

15. The delivery system of claim 14, wherein in the locked state, at least a portion of the structure abuts the secondary sheath proximal end, and wherein the structure comprises at least one flexible portion that locks to the secondary sheath in the locked state.

16. The delivery system of claim 15, wherein the sheath-locking section further comprises:
a taper defined in the secondary sheath proximal end; and
a slot defined in the secondary sheath proximal end, the slot disposed distal to the taper,
wherein the at least one flexible portion comprises a radial protrusion, and longitudinally translating the structure from the unlocked state to the locked state causes the at least one flexible portion to bend radially inward until the radial protrusion engages the slot.

17. The delivery system of claim 16, wherein:
the taper extends circumferentially within the secondary sheath lumen;
the slot extends circumferentially within the secondary sheath lumen; and
the at least one flexible portion comprises a plurality of flexible portions circumferentially disposed around the outer surface of the primary sheath.

18. The delivery system of claim 9, wherein:
the length reference section comprises an indicator window assembly disposed at the secondary sheath proximal end, the indicator window assembly comprising an indicator window assembly proximal end and an indicator window assembly distal end and comprising an indicator window assembly lumen from the indicator window assembly proximal end to the indicator window assembly distal end, the indicator window assembly lumen at least partially receiving the primary sheath; and
the indicator window assembly comprises at least a portion of the sheath-locking section.

19. The delivery system of claim 18, wherein the indicator window assembly comprises an indicator window through which the outer surface of the primary sheath is observable.

20. A method to deploy a prosthesis, the method comprising:
providing a primary sheath, a secondary sheath, and a prosthesis, where the primary sheath extends from a primary sheath distal end to a primary sheath proximal end and comprises a primary sheath lumen from the primary sheath distal end to the primary sheath proximal end, where the secondary sheath extends from a secondary sheath distal end to a secondary sheath proximal end and comprises a secondary sheath lumen from the secondary sheath distal end to the secondary sheath proximal end, and where the prosthesis has proximal and distal ends and is received within the primary sheath lumen adjacent to the primary sheath distal end in a contracted delivery state;
disposing the distal end of the secondary sheath adjacent to a proximal end of a receiving lumen of a vessel;
disposing the primary sheath within the secondary sheath lumen such that a length reference section disposed at the secondary sheath proximal end indicates a preselected length of the primary sheath distal end that extends distally out of the secondary sheath distal end during the contracted delivery state of the prosthesis, the preselected length corresponding to a preselected overlap with the vessel; and
longitudinally translating the primary sheath and the secondary sheath proximally relative to the prosthesis, wherein the longitudinally translating of the primary sheath and the secondary sheath proximally relative to the prosthesis transitions the prosthesis from the contracted delivery state to an expanded deployed state in which the prosthesis is received within the vessel and has the preselected overlap with the vessel.

* * * * *